US012806081B2

(12) United States Patent
Duensing

(10) Patent No.: US 12,806,081 B2
(45) Date of Patent: Nov. 24, 2026

(54) DEVICE AND METHOD FOR PLACEMENT AND REMOVAL OF A MENSTRUAL CUP

(71) Applicant: Madison Duensing, Saint Paul, MN (US)

(72) Inventor: Madison Duensing, Saint Paul, MN (US)

( * ) Notice: Subject to any disclaimer, the term of this patent is extended or adjusted under 35 U.S.C. 154(b) by 235 days.

(21) Appl. No.: 18/407,042

(22) Filed: Jan. 8, 2024

(65) Prior Publication Data

US 2024/0148565 A1 May 9, 2024

Related U.S. Application Data

(63) Continuation of application No. 16/850,563, filed on Apr. 16, 2020, now Pat. No. 11,883,266.

(60) Provisional application No. 62/834,557, filed on Apr. 16, 2019.

(51) Int. Cl.
*A61F 13/26* (2006.01)
*A61F 13/20* (2006.01)
*A61F 13/45* (2006.01)

(52) U.S. Cl.
CPC .......... *A61F 13/26* (2013.01); *A61F 13/2045* (2013.01); *A61F 2013/4562* (2013.01)

(58) Field of Classification Search
CPC .......... A61F 2013/4562; A61F 13/2045; A61F 5/4553; A61F 13/26–28
See application file for complete search history.

(56) References Cited

U.S. PATENT DOCUMENTS 3,835,856 A * 9/1974 Warncke ................. A61F 13/26 604/15
4,276,881 A 7/1981 Lilaonitkul
6,747,184 B2 6/2004 Zadini et al.
7,935,098 B2 5/2011 Bartning et al.
8,029,456 B2 10/2011 Fung
8,728,140 B2 5/2014 Feemster et al.
8,734,414 B2 5/2014 Winkel et al.
(Continued)

FOREIGN PATENT DOCUMENTS

CN 109833136 A * 6/2019
EP 616797 A1 9/1994
(Continued)

*Primary Examiner* — Susan S Su
(74) *Attorney, Agent, or Firm* — Harness, Dickey & Pierce, P.L.C.

(57) ABSTRACT

A device for placement and removal of a menstrual cup according to various aspects of the present disclosure includes an outer component and an inner component. The outer component extends along a longitudinal axis between first proximal and distal ends. The outer component includes a peripheral wall, a first interior region, and a protrusion. The peripheral wall includes an interior surface. The first interior region is at least partially defined by the peripheral wall. The protrusion extends from the interior surface toward the longitudinal axis. In certain aspects, the outer component includes an upper portion and a lower portion removably coupled to the upper portion. The inner component extends between a second proximal and distal ends. The inner component is disposed at least partially within the first interior region. The inner component is slidable along the longitudinal axis with respect to the outer component.

17 Claims, 18 Drawing Sheets

(56) References Cited

U.S. PATENT DOCUMENTS

| | | | |
|---|---|---|---|
| 9,993,371 B2 | 6/2018 | Kasper | |
| 2004/0078013 A1* | 4/2004 | Zunker .................. | A61F 2/005 604/355 |
| 2006/0213918 A1 | 9/2006 | Rajala et al. | |
| 2010/0312204 A1 | 12/2010 | Sheu | |
| 2012/0204410 A1 | 8/2012 | Mastalish et al. | |
| 2016/0296379 A1 | 10/2016 | Brown et al. | |
| 2017/0189222 A1 | 7/2017 | Lin | |

FOREIGN PATENT DOCUMENTS

| | | |
|---|---|---|
| FR | 2993773 A1 | 1/2014 |
| GB | 1199901 A | 7/1970 |
| KR | 101857956 B1 | 5/2018 |
| WO | WO-2018115546 A1 | 6/2018 |

* cited by examiner

IFig-22

DEVICE AND METHOD FOR PLACEMENT AND REMOVAL OF A MENSTRUAL CUP

CROSS-REFERENCE TO RELATED APPLICATIONS

This application is a continuation of U.S. application Ser. No. 16/850,563, filed on Apr. 16, 2020, which claims the benefit of U.S. Provisional Application No. 62/834,557, filed on Apr. 16, 2019. The entire disclosures of the above applications are incorporated herein by reference.

FIELD

The present disclosure relates to a device for placement and/or removal of a menstrual cup, and methods of using the device for placement and removal of a menstrual cup.

BACKGROUND

This section provides background information related to the present disclosure which is not necessarily prior art.

A menstrual cup is a reusable device that is inserted into a vagina. Menstrual cups are commonly used to collect menstrual fluid during menstruation. However, menstrual cups may also be used for other purposes, such as to alleviate pelvic cramps. A menstrual cup generally includes a body or cup portion that opens toward a uterus when positioned in the vagina, and stem extending from the body of the cup, which may be used to remove the menstrual cup from the vagina.

SUMMARY

This section provides a general summary of the disclosure and is not a comprehensive disclosure of its full scope or all of its features.

In various aspects, the present disclosure provides a device for placement and removal of a menstrual cup. The device includes an outer component and an inner component. The outer component extends along a longitudinal axis between a first proximal end and a first distal end. The outer component includes a peripheral wall, a first interior region, and a protrusion. The peripheral wall includes an interior surface. The first interior region is at least partially defined by the peripheral wall. The protrusion extends from the interior surface toward the longitudinal axis. The inner component extends between a second proximal end and a second distal end. The inner component is disposed at least partially within the first interior region. The inner component is slidable along the longitudinal axis with respect to the outer component.

In one aspect, the protrusion includes a first sloped surface. The first sloped surface defines a first angle with a plane substantially perpendicular to the longitudinal axis.

In one aspect, the first angle is greater than or equal to about 20° to less than or equal to about 75°.

In one aspect, the protrusion further includes a second sloped surface. The second slopped surface defines a second angle with the plane.

In one aspect, the second angle is greater than or equal to about 20° to less than or equal to about 65°.

In one aspect, the outer component comprises an upper portion and a lower portion. The lower portion is separable from the upper portion.

In one aspect, the upper portion includes a first plurality of threads. The lower portion includes a second plurality of threads. The first plurality of threads is configured to engage the second plurality of threads to couple the upper portion to the lower portion.

In one aspect, the upper portion includes the protrusion.

In one aspect, the protrusion defines an undercut into which the lower portion is at least partially disposed.

In one aspect, the second distal end includes a distal surface. The distal surface defines an aperture.

In one aspect, the inner component includes a wall. The wall defines a second interior region.

In one aspect, the inner component includes a first flange and a second flange. The first flange is disposed at the second distal end. The second flange is disposed at the second proximal end. The first flange is configured to prevent translation of the inner component with respect to the outer component in a first direction. The second flange is configured to prevent translation of the inner component with respect to the outer component in a second direction opposite the first direction.

In one aspect, the interior surface defines at least one of a plurality of indentations or a plurality of projections.

In one aspect, the outer component comprises a distal surface. The distal surface is at least one of chamfered or rounded.

In one aspect, the outer component includes a base. The base is disposed at the first proximal end. An outer surface of the base comprises at least one of a projection and an indentation.

In one aspect, the first proximal end defines a first dimension. The first distal end defines a second dimension. The second dimension is greater than the first dimension.

In one aspect, the peripheral wall comprises an outer surface. The outer surface defines a portion of an elliptic paraboloid.

In one aspect, the second distal surface defines a notch configured to receive at least a portion of the protrusion.

In various aspects, the present disclosure provides a device for placement and removal of a menstrual cup. The device includes an outer component and an inner component. The outer component extends along a longitudinal axis between a first proximal end and a first distal end. The outer component includes an upper portion and a lower portion. The upper portion includes the first distal end. The lower portion includes the first proximal end. The upper portion is removably coupled to the lower portion. The upper portion and the lower portion cooperate to form a peripheral wall. The peripheral wall at least partially defines an interior region. The inner component extends between a second proximal end and a second distal end. The inner component is disposed at least partially within the interior region. The inner component is slidable along the longitudinal axis with respect to the outer component.

In various aspects, the present disclosure provides a device for placement and removal of a menstrual cup. The device includes an outer component and an inner component. The outer component extends along a longitudinal axis between a first proximal end and a first distal end. The outer component includes an upper portion and a lower portion. The upper portion includes the first distal end. The upper portion further includes a projection. The projection extends from a surface toward the longitudinal axis. The lower portion is removably coupled to the upper portion. The lower portion includes the first proximal end. The lower portion cooperates with the upper portion to form a peripheral wall. The peripheral wall at least partially defines an interior region. The inner component is disposed at least partially within the interior region and slidable along the longitudinal axis with respect to the outer component. The inner component includes a substantially cylindrical wall, a first flange, and a second flange. The substantially cylindrical wall extends along the longitudinal axis. The first flange includes a second distal end and a distal surface. The distal surface defines an aperture. The second flange includes a second proximal end.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

FIG. 13A shows the menstrual cup in an expanded configuration; and FIG. 13B shows the menstrual cup in a collapsed configuration;

Figure 13A:
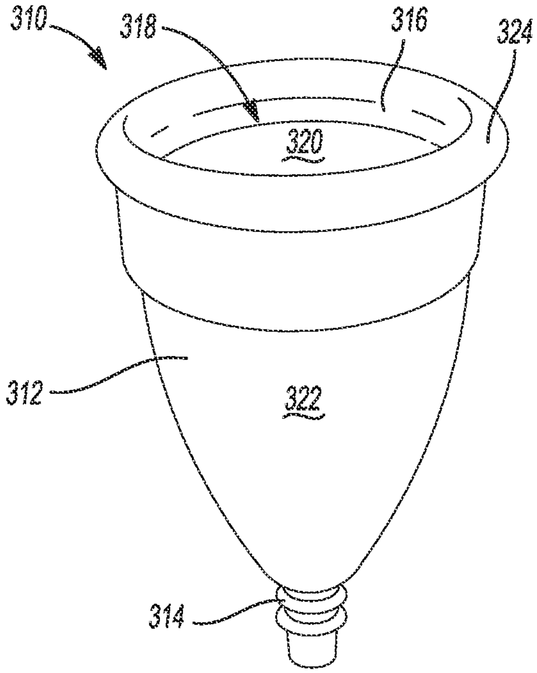
FIGS. 13A-13B are perspective views of a menstrual cup according to various aspects of the present disclosure.
Figure 13B:
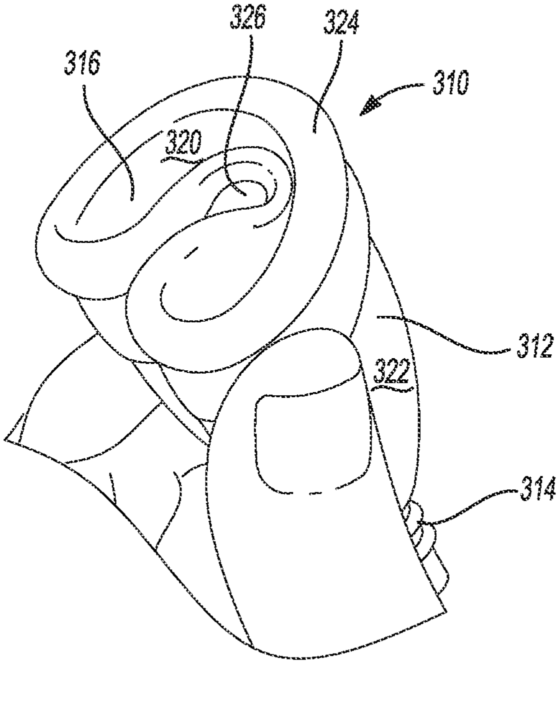
Figure 14:
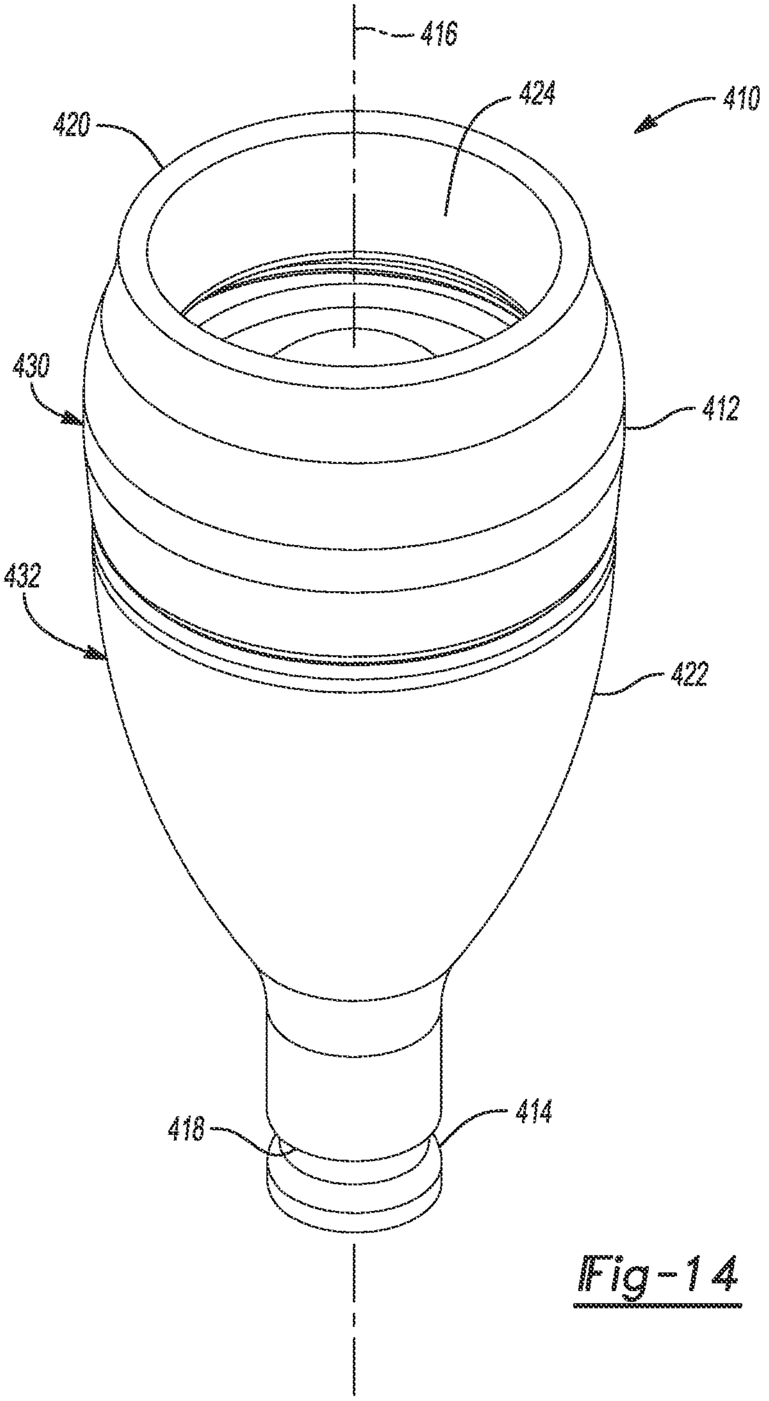
FIG. 14 is a perspective view of another device for placement and removal of a menstrual cup according to various aspects of the present disclosure, the device being in a plunged configuration.
Figure 25A:
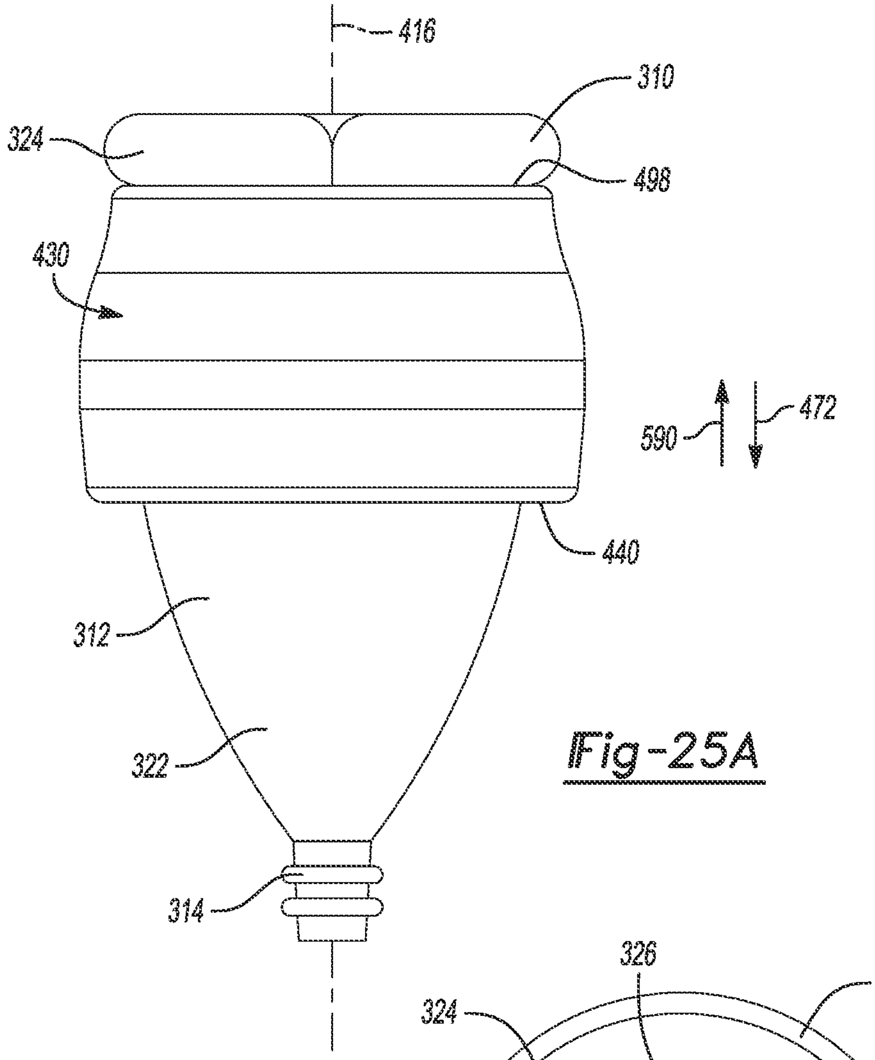
Figure 25B:
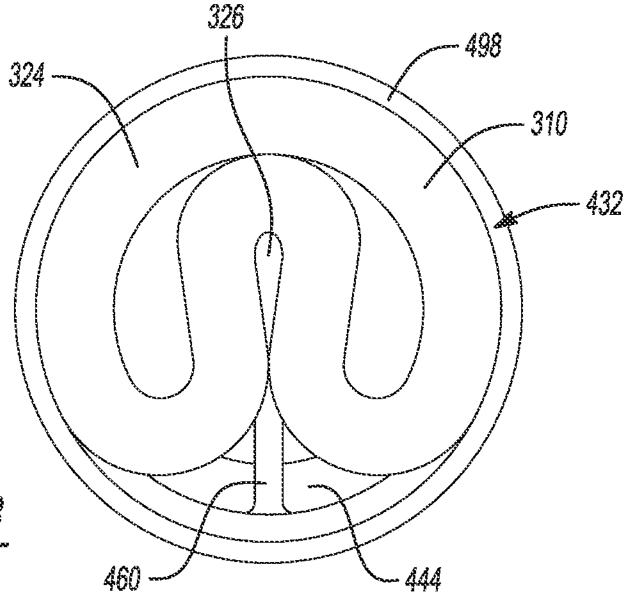
Figure 25C:
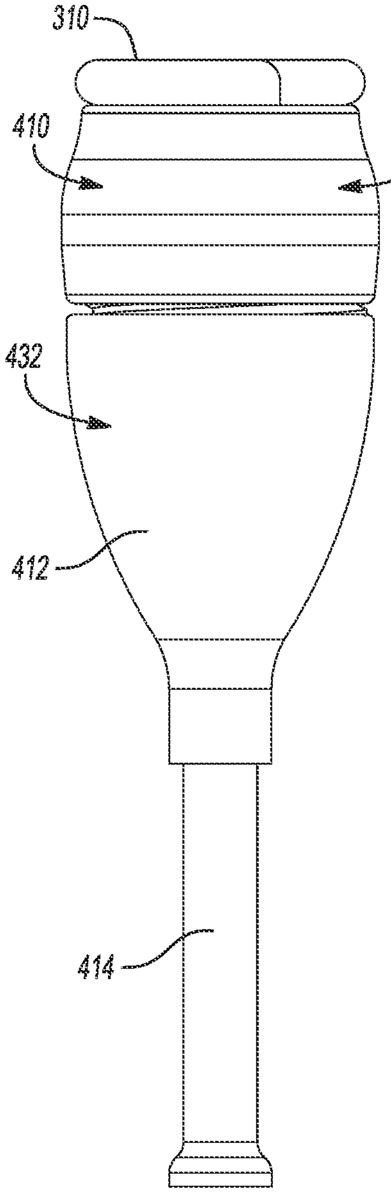
Figure 25D:
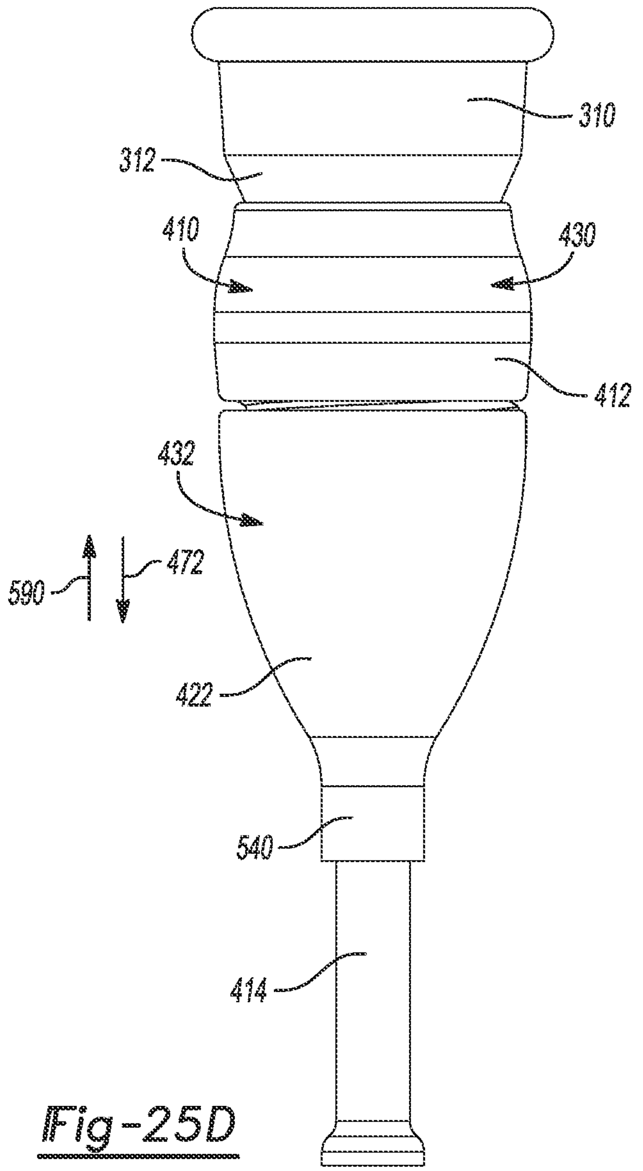
Figure 25E:
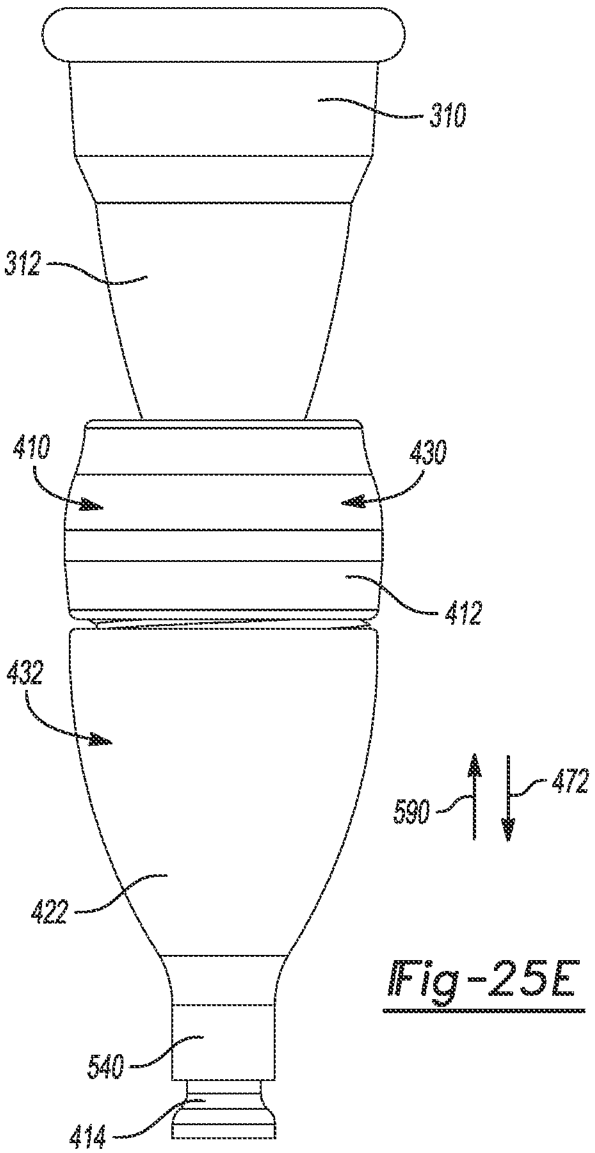
Figure 26:
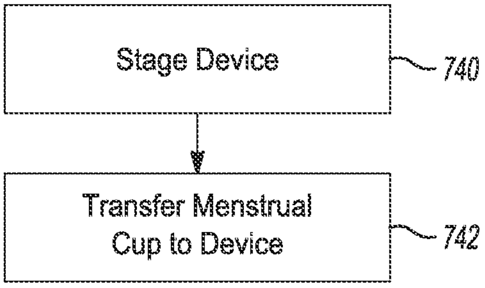

FIGS. 25A-25E depict a method of using the device of FIG. 14 for placement and removal of the menstrual cup of FIGS. 13A-13B; FIG. 25A is a perspective view of the device in the extended configuration and the menstrual cup in the collapsed configuration; FIG. 25B is a perspective view of the device in an intermediate configuration and the menstrual cup in an intermediate configuration; FIG. 25C is a perspective view of the device in the plunged configuration and the menstrual cup in the expanded configuration; FIG. 25D is a perspective view of the upper portion of the outer component having the menstrual cup disposed therein, the menstrual cup being in the collapsed configuration; and FIG. 25E is a top view of the upper portion and menstrual cup of FIG. 25D; and FIG. 26 is a flowchart depicting a method of removing the menstrual cup of FIG. 13 using the device of FIG. 14 according to various aspects of the present disclosure.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Disposable feminine hygiene products, such as tampons and pads, absorb menstrual fluid and are subsequently discarded. Menstrual cups collect menstrual fluid and, in contrast, may be reused. During typical use, a menstrual cup is manually folded or collapsed (see, e.g., FIG. 13B) by a user for placement in the vagina. Once the menstrual cup is placed in the vagina, it shifts to an expanded configuration (see, e.g., FIG. 13A) to collect menstrual fluid. After use, the menstrual cup is removed, such as by manually pulling the stem and partially collapsing the menstrual cup to reduce suction and resistance to removal. After removal, the menstrual cup can be cleaned and reused. Accordingly, the use of menstrual cups may have a lower long-term cost and a decreased environmental impact compared to disposable feminine hygiene products.

Despite the advantages of using menstrual cups, some users still prefer the convenience of disposable feminine hygiene products. For example, manual methods of placing and removing or replacing menstrual cups may deter the use of menstrual cups, particularly in public places where access to privacy and hygienic spaces is more limited. Additionally, manual placement and removal may be more time-consuming than the use of disposable feminine hygiene products, deterring the use of menstrual cups on-the-go. Accordingly, it would be desirable to improve ease of use of menstrual cups.

In various aspects, the present disclosure provides a reusable device for placement and/or removal of a menstrual cup. The device includes an outer tube and a plunger that is slidable with respect to the outer tube. Prior to placement of the menstrual cup, the user stages the menstrual cup within at least a portion of the outer tube. During staging, the menstrual cup slides into the outer tube and engages a protrusion on the outer tube, causing the menstrual cup to shift into a collapsed configuration. To place the menstrual cup, the user transfers the menstrual cup from the outer tube into the vagina by sliding the plunger with respect to the outer tube. To remove the menstrual cup, the user grasps a stem of the menstrual cup with the plunger to pull the menstrual cup into the outer tube. As the menstrual cup slides into the outer tube, it engages the protrusion to at least partially collapse, which reduces suction and facilitates removal. Both the menstrual cup and the device are reusable. The device may increase ease of use of a menstrual cup, particularly during placement and/or removal of the menstrual cup in public places. In certain aspects, the device may be universal such that it may be used with various sizes and shapes of menstrual cups.

Figure 1:
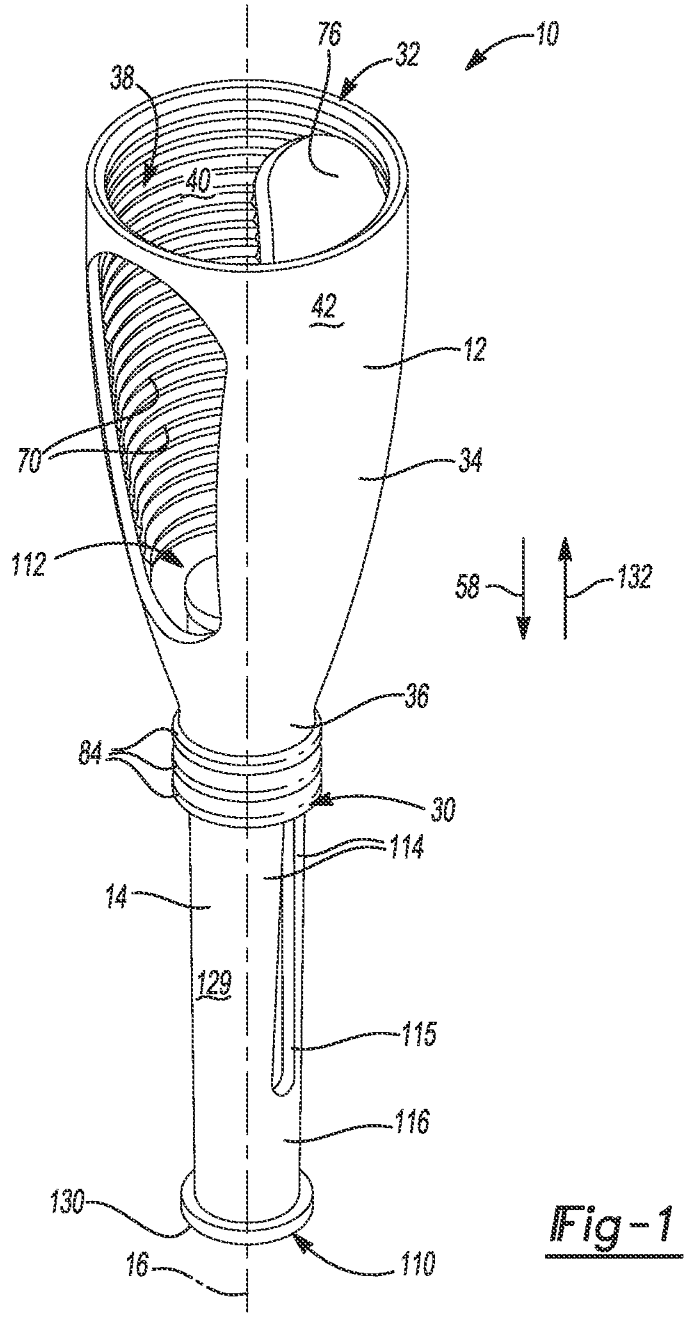
FIG. 1 is a perspective view of a device for placement and removal of a menstrual cup according to various aspects of the present disclosure, the device being shown in an extended configuration.

With reference to FIGS. 1-4, an assembly or device 10 for placement and/or removal of a menstrual cup (see, e.g., menstrual cup 310 of FIGS. 13A-13B) according to various aspects of the present disclosure is provided. The device 10 includes an outer component or outer tube 12, and an inner component or plunger 14. At least one of the outer tube 12 and the plunger 14 is translatable along a longitudinal axis 16 with respect to the other of the outer tube 12 and the plunger 14. The device 10 is movable between a plunged configuration (FIGS. 2-4) and an extended configuration (FIG. 1). The device 10 can be used for both placement of the menstrual cup in a vagina and removal of the menstrual cup from the vagina. However, it will be appreciated that similar devices may be used for only placement or only removal.

Figure 5:
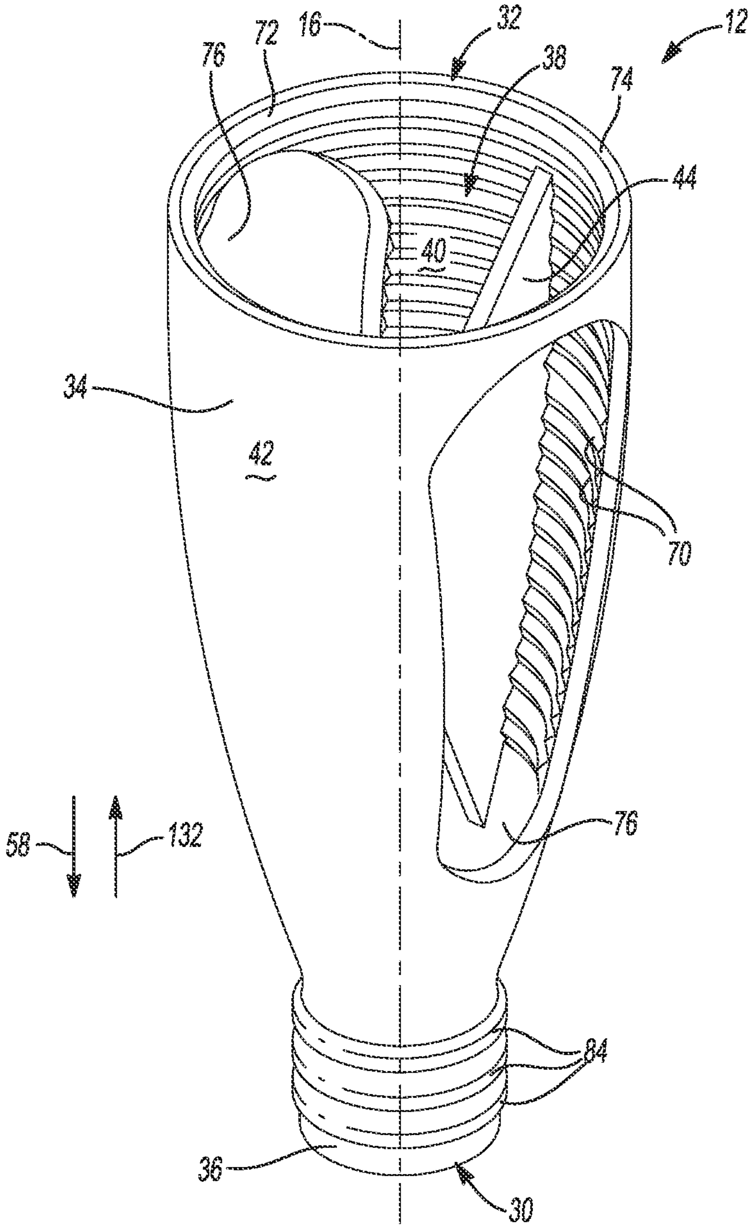
FIG. 5 is a perspective view of an outer component of the device of FIG. 1.
Figure 7:
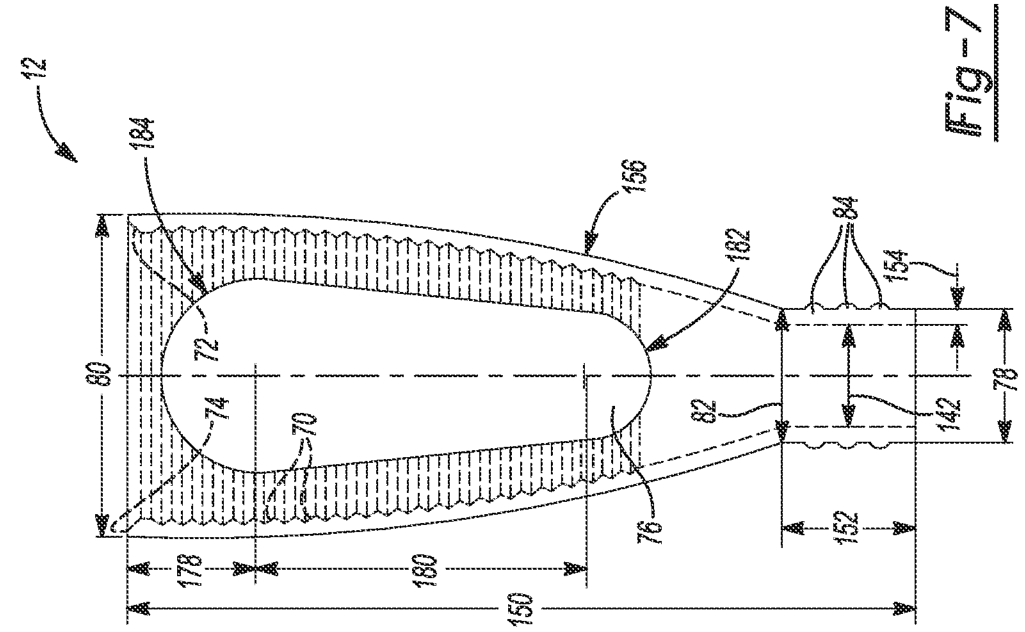
FIG. 7 is another cross-sectional view of the outer component of FIG. 5.
Figure 6:
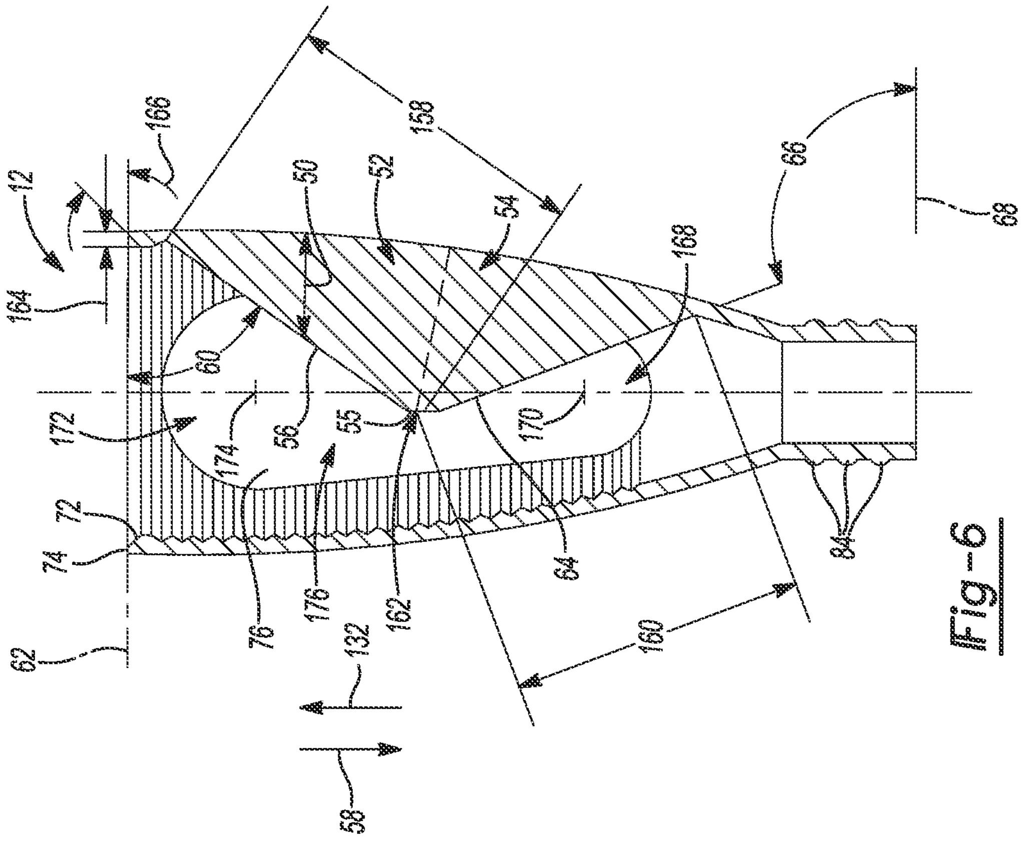
FIG. 6 is a cross-sectional view of the outer component of FIG. 5.

Referring to FIGS. 5-7, the outer tube 12 extends between a first proximal end 30 and a first distal end 32. The outer tube 12 includes a peripheral wall 34. The outer tube 12 may further include a first base 36 that is disposed adjacent to the first proximal end 30. The peripheral wall 34 may extend between the first base 36 and the first distal end 32. During placement and removal of the menstrual cup, a user may grip the outer tube 12 at the first base 36 and/or the peripheral wall. In certain aspects, the user may at least partially insert the first distal end 32 into the vagina during placement of the menstrual cup. However, in various other aspects, an outer tube remains outside of the vagina during placement and removal.

The outer tube 12 further includes a hollow interior region 38. The hollow interior region 38 is at least partially defined by the peripheral wall 34. The longitudinal axis 16 extends through the hollow interior region 38. The hollow interior region 38 is configured to receive at least a portion of the menstrual cup when the device 10 is in the extended configuration.

The peripheral wall 34 includes an interior surface 40 and an exterior surface 42. The interior surface 40 is disposed closer to the longitudinal axis 16 than the exterior surface 42. The interior surface 40 is in communication with the hollow interior region 38.

The outer tube 12 may further include a protrusion 44. The protrusion 44 extends from the interior surface 40 of the peripheral wall 34 toward the longitudinal axis 16. The protrusion 44 may extend along at least a portion of a length of the peripheral wall 34 (i.e., substantially parallel to the longitudinal axis 16). For example, the protrusion 44 may extend along greater than or equal to about 20%, optionally greater than or equal to about 30%, optionally greater than or equal to about 40%, optionally greater than or equal to about 50%, optionally greater than or equal to about 60%, optionally greater than or equal to about 70%, optionally greater than or equal to about 80%, optionally greater than or equal to about 90%, or optionally greater than or equal to about 95% of a length of the peripheral wall. In certain alternative aspects, the protrusion 44 may extend along substantially the entire length of the peripheral wall 34 (not shown). In certain aspects, an outer tube may include more than one separable portion and the protrusion may be included on only one of the portions (see, e.g., protrusion 460 of FIGS. 15-16).

The protrusion 44 is configured to engage the menstrual cup. More particularly, when the menstrual cup is pulled into the device 10, the protrusion 44 may engage the menstrual cup to at least partially collapse the menstrual cup so that the menstrual cup is in an intermediate configuration (see, e.g., FIG. 25D, depicting menstrual cup 310 in device 410) or a collapsed configuration (see, e.g., FIGS. 25A-25C, depicting menstrual cup 310 in upper portion 430 of device). When the menstrual cup is ejected from the device 10, the menstrual cup may disengage the protrusion 44 to shift into the expanded configuration (see, e.g., FIG. 25E, depicting menstrual cup 310 in device 410).

In certain aspects the protrusion 44 may be sized and shaped to gradually collapse and/or expand the menstrual cup. For example, as best shown in FIG. 6, the protrusion 44 may include a radial dimension 50 (i.e., perpendicular to the longitudinal axis 16 and parallel to a radius of the tube 12) that varies along the longitudinal axis 16. In certain aspects, the protrusion 44 may include a first portion 52, a second portion 54, and an apex 55 disposed between the first and second portions 52, 54. The protrusion 44 may be substantially triangular. In some examples, both the first and second portions 52, 54 of the protrusion 44 may be right triangle shaped.

The first portion 52 may include a first sloped surface 56. The radial dimension 50 may increase in a first direction 58 on the first portion 52. The first direction 58 may be defined by a vector extending substantially parallel to the longitudinal axis 16, from the first distal end 32 to the first proximal end 30.

The first sloped surface 56 may be configured to slidingly engage the menstrual cup during placement and removal of the menstrual cup. The first sloped surface 56 may form a first angle 60 with a first plane 62 that extends substantially perpendicular to the longitudinal axis 16. The first angle 60 may be greater than or equal to about 35° to less than or equal to about 75° (e.g., greater than or equal to about 35° to less than or equal to about 40°, greater than or equal to about 40° to less than or equal to about 45°, greater than or equal to about 45° to less than or equal to about 50°, greater than or equal to about 50° to less than or equal to about 55°, greater than or equal to about 55° to less than or equal to about 60°, greater than or equal to about 60° to less than or equal to about 65°, or greater than or equal to about 65° to less than or equal to about 70°). In some examples, the first angle 60 may be greater than or equal to about 40° to less than or equal to about 70°, optionally greater than or equal to about 45° to less than or equal to about 65°, optionally greater than or equal to about 50° to less than or equal to about 60°, or optionally about 55°.

In certain variations, the second portion 54 of the protrusion 44 includes a second sloped surface 64. The radial dimension 50 of the protrusion 44 may decrease in the first direction 58 on the second portion 54. The second sloped surface 64 may form a second angle 66 with a second plane 68 substantially perpendicular to the longitudinal axis 16. The second angle 66 may be greater than or equal to about 90° to less than or equal to about 130° (e.g., greater than or equal to about 90° to less than or equal to about 95°, greater than or equal to about 95° to less than or equal to about 100°, greater than or equal to about 100° to less than or equal to about 105°, greater than or equal to about 105° to less than or equal to about 110°, greater than or equal to about 110° to less than or equal to about 115°, greater than or equal to about 115° to less than or equal to about 120°, or greater than or equal to about 120° to less than or equal to about 125°, or greater than or equal to about 125° to less than or equal to about 130°). In some examples, the second angle 66 may be greater than or equal to about 95° to less than or equal to about 125°, optionally greater than or equal to about 100° to less than or equal to about 120°, optionally greater than or equal to about 105° to less than or equal to about 115°, or optionally about 110°. In various aspects, the second sloped surface 64 and rounded shape of the apex 55 may facilitate removal of the menstrual cup from the outer tube 12 without inhibiting translation of the menstrual cup along the longitudinal axis 16.

The interior surface 40 of the peripheral wall 34 is configured to engage the menstrual cup as the menstrual cup slides in and out of the device 10. In certain aspects, the interior surface 40 may define a plurality of indentations 70, which may be a plurality of circumferential grooves. The indentations 70 may repeat along at least a portion of the length of the peripheral wall 34. Presence of the indentations 70 reduces a contact area of the interior surface 40 that will engage the menstrual cup. The reduction in contact area facilitates sliding of the menstrual cup along the interior surface 40. In various alternative aspects, the indentations may define other shapes or configurations on the interior surface. For example, the indentations may define a plurality of axial grooves, a plurality of dimples, knurling, or combinations thereof (not shown). In various alternative aspects, the interior surface 40 may include a plurality of projections rather than indentations to facilitate sliding of the menstrual cup over the interior surface 40.

The indentations 70 may be present over a portion of an area of the interior surface 40, as shown. For example, the indentations 70 may be present only where the menstrual cup is expected to engage the interior surface 40. In certain aspects, the portion may be greater than or equal to about 20% to less than or equal to about 100% (e.g., greater than or equal to about 20% to less than or equal to about 30%, greater than or equal to about 30% to less than or equal to about 40%, greater than or equal to about 40% to less than or equal to about 50%, greater than or equal to about 50% to less than or equal to about 60%, greater than or equal to about 60% to less than or equal to about 70%, greater than or equal to about 70% to less than or equal to about 80%, greater than or equal to about 80% to less than or equal to about 90%, greater than or equal to about 90% to less than or equal to about 100%). In various alternative aspects, the indentations 70 may extend over substantially the entire area of the interior surface 40. In various alternative aspects, an interior surface is substantially smooth and uninterrupted.

The first distal end 32 may include a chamfer 72 between the interior surface 40 and a first distal surface 74. The presence of the chamfer 72 may facilitate an easier transition of the menstrual cup into the outer tube 12. The first distal end 32 may also include one or more additional features to facilitate placement of the first distal end 32 into the vagina and/or increase comfort for the user. For example, in various alternative aspects, the first distal end 32 may include a rounded corner or chamfer between the exterior surface 42 and the first distal surface 74 (not shown). In various alternative aspects, the first distal surface 74 may be a smooth curved surface extending between the exterior surface 42 and the interior surface 40.

The peripheral wall 34 may include one or more elongated apertures 76. The elongated apertures 76 may provide access to the hollow interior region 38 from outside of the outer tube 12. More particularly, the elongated apertures 76 may provide a passage for the user to grasp the plunger 14 when the device 10 is in the plunged configuration.

A quantity of elongated apertures 76 may be two, as shown. The elongated apertures 76 may include a pair of opposing elongated apertures 76. In various alternative aspects, the peripheral wall 34 may include other quantities of elongated apertures 76. For example, the peripheral wall 34 may include a single elongated aperture, three elongated apertures, or four elongated apertures. It may be advantageous to include greater than two elongated apertures so that the user can grab the plunger through the elongated apertures from a desired angle, thereby improving ease of use of the device. In various alternative aspects, the elongated apertures 76 can be omitted, such as when it is possible for the user to adequately grasp the plunger 14 and/or menstrual cup from the outer tube 12.

The elongated apertures 76 may be sized and shaped to permit the user's fingers to at least partially pass through the elongated apertures 76 to grasp the plunger 14. In certain aspects, each elongated aperture 76 may occupy an individual aperture percentage of the peripheral wall. The individual aperture percentage is a percentage of surface area (aligned with the exterior surface 42) occupied by the elongated aperture 76, compared to an area of the exterior surface 42 without any elongated apertures 76. The individual aperture percentage may be greater than or equal to about 10% to less than or equal to about 75% (e.g., greater than or equal to about 10% to less than or equal to about 20%, greater than or equal to about 20% to less than or equal to about 30%, greater than or equal to about 30% to less than or equal to about 40%, greater than or equal to about 40% to less than or equal to about 50%, greater than or equal to about 50% to less than or equal to about 60%, greater than or equal to about 60% to less than or equal to about 75%).

The outer tube 12 may define a substantially circular cross section. More particularly, the peripheral wall 34 and the first base 36 may each define a substantially circular cross section. A diameter of the substantially circular cross section may vary along the longitudinal axis 16. As best shown in FIG. 7, the first proximal end 30 may define a first dimension 78 (e.g., a proximal diameter), and the first distal end 32 may define a second dimension 80 (e.g., a distal diameter). An intersection between the peripheral wall 34 and the first base 36 may define a third dimension 82 (e.g., an intersection diameter).

The second dimension 80 may be greater than the first dimension 78. In certain aspects, the first base 36 may define a substantially cylindrical shape, so that the first dimension 78 and the third dimension 82 are substantially the same. In various alternative aspects, the first and third dimensions 78, 82 may be different and/or the first base 36 may be non-cylindrical. In certain aspects, the peripheral wall 34 may define a portion of an elliptic paraboloid shape, with the second dimension 80 being greater than the third dimension 82.

In various alternative aspects, the peripheral wall 34 and first base 36 may define other shapes. In one example, the peripheral wall 34 is substantially frusto-conical. In another example, the peripheral wall 34 is substantially cylindrical (not shown). In yet other examples, one or both of the peripheral wall 34 and the first base 36 have non-circular cross sections (e.g., substantially triangular, square, pentagonal, hexagonal, heptagonal, octagonal, nonagonal, or decagonal). Although interior and exterior surfaces 40, 42 are shown as having substantially the same cross-sectional shapes with respect to the longitudinal axis 16 (i.e., circular), they may alternatively define different cross-sectional shapes. In one example, the interior surface 40 defines a substantially octagonal cross section, and the exterior surface 42 defines a substantially circular cross section.

The first base 36 may include a plurality of projections 84, such as a plurality of circumferential ribs. The projections 84 may reduce slipping when a user grasps the first base 36. The projections 84 may additionally or alternatively include other features to facilitate gripping, such as knurling, a plurality of round projections, an axial waveform pattern, threads, or combinations thereof, by way of example (not shown). In various alternative aspects, the first base 36 may include a plurality of indentations rather than projections to facilitate gripping (not shown). In various aspects, a device additionally or alternatively includes gripping features on a peripheral wall.

With reference to FIGS. 8-12, the plunger 14 extends between a second proximal end 110 and a second distal end 112. The plunger 14 includes two or more arms, such as a first arm 114-1 and a second arm 114-2 (collectively referred to as the "arms 114"). The first and second arms 114-1, 114-2 are separated by a gap 115. At least one of the first arm 114-1 and the second arm 114-2 is movable with respect to the other of the first arm 114-1 and the second arm 114-2 to reduce a magnitude of the gap 115. As will be described in greater detail below, the arms 114 can be pinched together toward the longitudinal axis 16 to grip a stem of the menstrual cup. The arms 114 are therefore movable between an open configuration (i.e., separated at the second distal end 112) and closed configuration (i.e., engaging one another and/or the menstrual cup at the second distal end 112). In various alternative aspects, the plunger 14 may include greater than two arms, with at least an end of each arm being configured to translate radially inward toward the longitudinal axis 16 to pinch the stem. In various alternative aspects, a plunger may have a single-piece unitary structure without movable arms (see, e.g., plunger 414 of FIGS. 19-20).

Figure 8:
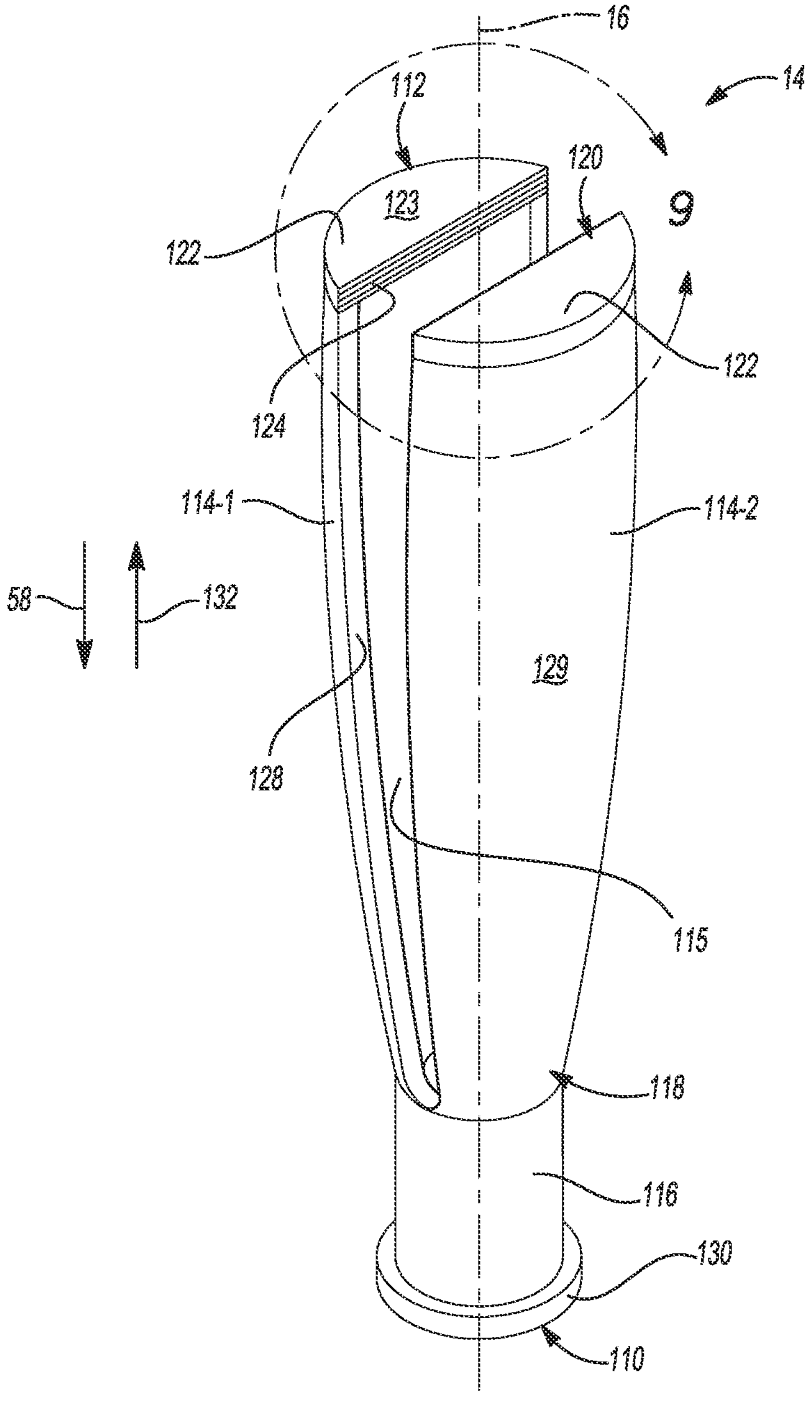
FIG. 8 is a perspective view of an inner component of the device of FIG. 1.

The plunger 14 may further include a second base 116 that is disposed at the second proximal end 110. The arms 114 may extend from the second base 116 to the second distal end 112 of the plunger 14. Each of the arms 114 may be fixed at the second base 116 and free at the second distal end 112. Accordingly, each of the arms 114 may include a fixed end 118 and a free end 120 (FIG. 8). In certain aspects, the first and second arms 114-1, 114-2 may be mirror images of one another with respect to a plane including the longitudinal axis 16. In various alternative aspects, a plunger may include at least two arms that are free at both ends so that the plunger is free of a base. The two arms may be coupled to one another, such as by a spring.

In certain aspects, each of the arms 114 may include a plate 122 disposed at the free end 120. In certain aspects, each plate 122 may define a circle segment substantially perpendicular to the longitudinal axis 16. The plates 122 may cooperate to form a portion of a circle perpendicular to the longitudinal axis when the plunger 14 is in the open condition. Each plate 122 may include a second distal surface 123. Those skilled in the art will appreciate that the plates 122 may have other shapes.

Each plate 122 may further include a grip surface 124. The grip surfaces 124 may face one another with the longitudinal axis 16 extending between the grip surfaces 124. Each of the grip surface 124 may include one or more ribs 126. The presence of the ribs 126 may increase pressure on the stem of the menstrual cup when the plunger 14 grips the stem in the closed configuration. In various alternative aspects, the grip surfaces 124 may additionally or alternatively include protrusions having other shapes and orientations (e.g., a chevron-shaped protrusions). In various alternative aspects, the arms 114 may include grip surfaces, but be free of plates that extend substantially perpendicular to the longitudinal axis 16 (e.g., having a shape similar to tweezers) (not shown).

Each arm 114 includes an arm wall 128 having an outer surface 129. In certain aspects, the arm walls 128 are convex with respect to the longitudinal axis 16. Each arm wall 128 may therefore define an open region. The convex shape of the arm walls 128 may facilitate gripping of the plunger through the elongated apertures 76. However, other shapes of arm walls 128 are contemplated. In one example, the arm walls 128 are substantially planar (not shown). In another example, the arm walls 128 include curvature in a radial direction, but not in a circumferential direction.

Figure 2:
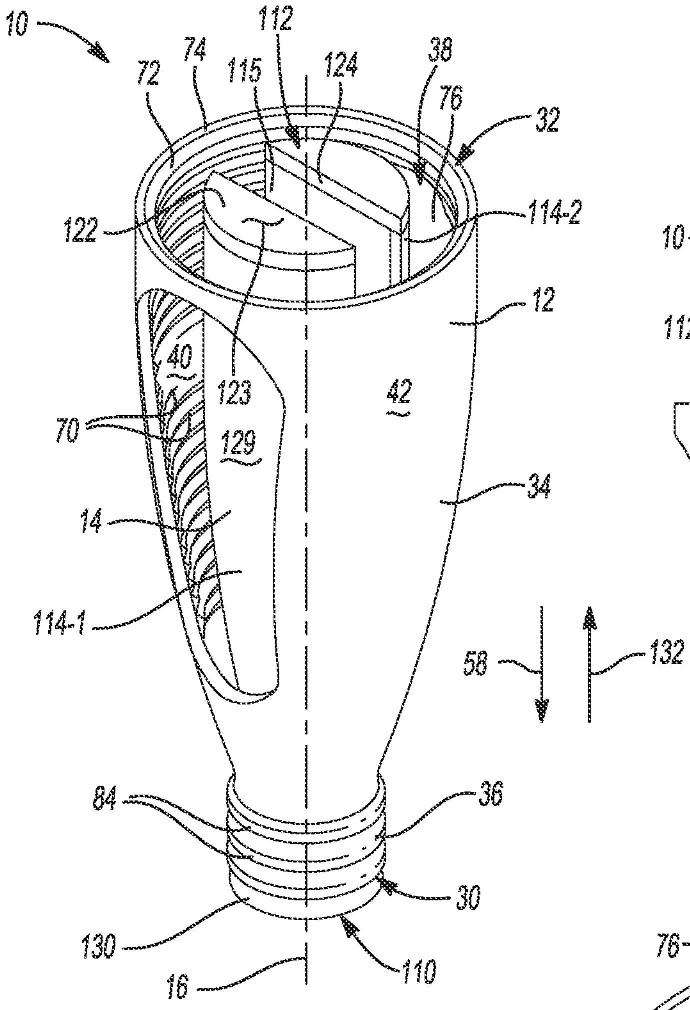
FIG. 2 is a perspective view of the device of FIG. 1, the device being shown in a plunged configuration.
Figure 3:
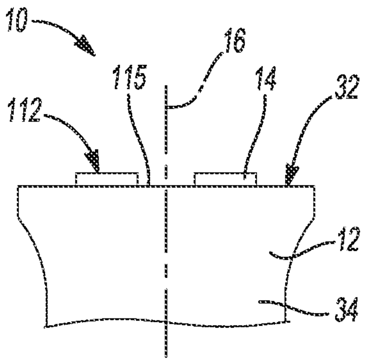
FIG. 3 is a partial side view of the device of FIG. 2.
Figure 4:
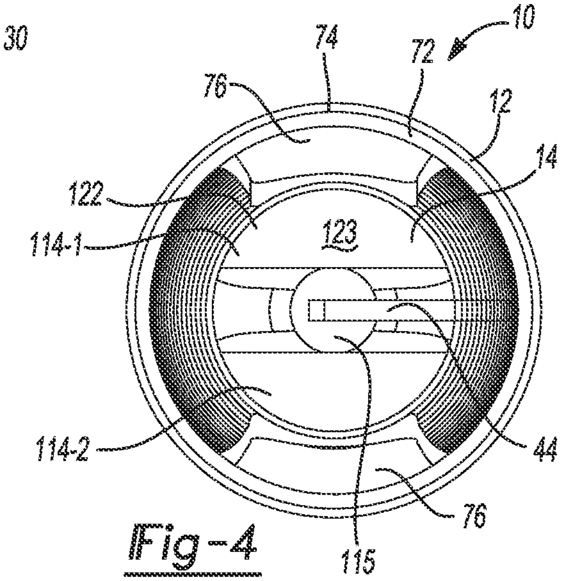
FIG. 4 is a top view of the device of FIG. 2.

In certain aspects, the second base 116 includes an outwardly-extending lip 130. The lip 130 may be disposed at the second proximal end 110. The lip 130 may extend outwardly (e.g., radially outwardly when the second base 116 has a substantially circular cross section) from the second base 116. The lip 130 may extend around substantially an entire circumference of the second base 116. In various alternative aspects, the lip 130 may extend around only a portion of the circumference of the second base 116 (e.g., as a single protrusion or a plurality of protrusions). As best shown in FIG. 2, the lip 130 may be configured to engage the first base 36 of the outer tube 12 to limit axial translation of the plunger 14 in a second direction 132 opposite the first direction 58. More particularly, engagement of the lip 130 with the first base 36 may prevent the second base 116 from translating past the first base 36 in the second direction 132.

The plunger 14 may be prevented from translating past a predetermined axial position in the first direction 58 based on dimensions of the plunger 14. More particularly a fourth dimension 140 (e.g., maximum outer dimension of the second distal end 112 substantially perpendicular to the longitudinal axis 16) (FIG. 10) of the plate 122 may be greater than a fifth dimension 142 (e.g., inner diameter) (FIG. 7) of the second base 116. Accordingly, the arm walls 128 may be configured to engage the peripheral wall 34 and or the first base 36 to limit translation of the plunger 14 with respect to the outer tube 12 in the first direction 58. In various alternative aspects, motion of the plunger 14 in the first direction 58 with respect to the outer tube 12 may be limited by engagement of a radially-outwardly extending protrusion on the second distal end 112 of the plunger 14 with a radially-inwardly extending protrusion (not shown) on the first base 36 of the outer tube 12.

Returning to FIGS. 3-4, when the device 10 is in the plunged configuration, a portion of the protrusion 44 of the outer tube 12 is disposed in the gap 115 between the arms 114. However, the gap 115 remains open at the second distal end 112 so that the arms 114 are free to engage the menstrual cup. In certain aspects, the second distal end 112 may project outside of the outer tube 12 in the second direction 132 beyond the first distal surface 74. In various alternative aspects, the first and second distal surfaces 74, 112 may be flush with one another, or the second distal surface 123 may be recessed with respect to the first distal surface 74.

The device 10 may define various sizes and shapes. Example dimensions are described below. However, one skilled in the art will appreciate that devices according to various aspects of the present disclosure may have different dimensions, depending at least on size and style of menstrual cup. Returning to FIG. 7, the outer tube 12 may define a first height 150 substantially perpendicular to the longitudinal axis 16. The first height 150 is a sum of a second height (not shown) of the peripheral wall and a third height 152 of the first base 36. In certain aspects, the first height 150 may be greater than or equal to about 2 inches to less than or equal to about 5 inches. The third height 152 may be greater than or equal to about 0.5 inch to less than or equal to about 1.5 inches (e.g., greater than or equal to about 0.5 inch to less than or equal to about 0.75 inch, greater than or equal to about 0.75 inch to less than or equal to about 1.0 inch, greater than or equal to about 1.0 inch to less than or equal to about 1.25 inches, or greater than or equal to about 1.25 inches to less than or equal to about 1.5 inches). The peripheral wall 34 and the first base 36 may have a first thickness 154. The first thickness 154 may be greater than or equal to about 0.03125 inch to less than or equal to about 0.25 inch (e.g., greater than or equal to about 0.03125 inch to less than or equal to about 0.0625 inch, greater than or equal to about 0.0625 inch to less than or equal to about 0.09375 inch, greater than or equal to about 0.09375 inch to less than or equal to about 0.125 inch, greater than or equal to about 0.125 inch to less than or equal to about 0.15625 inch, greater than or equal to about 0.15625 inch to less than or equal to about 0.1875 inch, greater than or equal to about 0.1875 inch to less than or equal to about 0.21875 inch, greater than or equal to about 0.21875 inch to less than or equal to about 0.25 inch). In various alternative aspects, the peripheral wall 34 and the first base 36 may have different wall thicknesses.

As described above, the outer tube 12 may have the first dimension 78 (at the first proximal end 30), the second dimension 80 (at the first distal end 32), and the third dimension 82 (between the peripheral wall 34 and the first base 36) substantially perpendicular to the longitudinal axis 16. In certain aspects, the first dimension 78 may be greater than or equal to about 0.25 inch to less than or equal to about 1 inch (e.g., greater than or equal to about 0.25 inch to less than or equal to about 0.5 inch, greater than or equal to about 0.5 inch to less than or equal to about 0.75 inch, greater than or equal to about 0.75 inch to less than or equal to about 1 inch). The second dimension 80 may be greater than or equal to about 0.75 inch to less than or equal to about 1.5 inches (e.g., greater than or equal to about 0.75 inch to less than or equal to about 1 inch, greater than or equal to about 1 inch to less than or equal to about 1.25 inches, greater than or equal to about 1.25 inches to less than or equal to about 1.5 inches). The third dimension 82 may be greater than or equal to about 0.75 inch to less than or equal to about 1.5 inches (e.g., greater than or equal to about 0.75 inch to less than or equal to about 1 inch, greater than or equal to about 1 inch to less than or equal to about 1.25 inches, greater than or equal to about 1.25 inches to less than or equal to about 1.5 inches).

The exterior surface 42 of the peripheral wall 34 may define a first diameter of curvature 156. In certain aspects, the first diameter of curvature 156 may be greater than or equal to about 10 inches to less than or equal to about 15 inches (e.g., greater than or equal to about 10 inches to less than or equal to about 11 inches, greater than or equal to about 11 inches to less than or equal to about 12 inches, greater than or equal to about 12 inches to less than or equal to about 13 inches, greater than or equal to about 13 inches to less than or equal to about 14 inches, greater than or equal to about 14 inches to less than or equal to about 15 inches).

The protrusion 44 may define a thickness that is substantially the same as the first thickness 154 of the peripheral wall 34 and the first base 36. With reference to FIG. 6, the first portion 52 of the protrusion 44 defines a first length 158 (e.g., a length of the first sloped surface 56). In certain aspects, the first length 158 may be greater than or equal to about 0.5 inch to less than or equal to about 2 inches (e.g., greater than or equal to about 0.5 inch to less than or equal to about 1 inch, greater than or equal to about 1 inch to less than or equal to about 1.5 inches, or greater than or equal to about 1.5 inches to less than or equal to about 2 inches). The second portion 54 of the protrusion 44 defines a second length 160 (e.g., a length of the second sloped surface 64). In certain aspects, the second length 160 may be greater than or equal to about 0.5 inch to less than or equal to about 2 inches (e.g., greater than or equal to about 0.5 inch to less than or equal to about 1 inch, greater than or equal to about 1 inch to less than or equal to about 1.5 inches, or greater than or equal to about 1.5 inches to less than or equal to about 2 inches). The apex 55 defines a first radius of curvature 162. In certain aspects, the first radius of curvature 162 may be greater than or equal to about 0.125 inch to less than or equal to about 0.5 inch (e.g., greater than or equal to about 0.125 inch to less than or equal to about 0.25 inch, greater than or equal to about 0.25 inch to less than or equal to about 0.375 inch, or greater than or equal to about 0.375 inch to less than or equal to about 0.5 inch).

The chamfer 72 defines a sixth dimension 164 in a direction substantially perpendicular to the longitudinal axis 16. The chamfer 72 defines a third angle 166 between the first distal surface 74 and the interior surface 40. In certain aspects, the sixth dimension 164 may be greater than or equal to about 0.0625 inch to less than or equal to about 0.25 inch (e.g., greater than or equal to about 0.0625 inch to less than or equal to about 0.125 inch, greater than or equal to about 0.125 inch to less than or equal to about 0.1875 inch, or greater than or equal to about 0.1875 inch to less than or equal to about 0.25 inch). The third angle 166 may be greater than or equal to about 10° to less than or equal to about 80° (e.g., greater than or equal to about 10° to less than or equal to about 20°, greater than or equal to about 20° to less than or equal to about 30°, greater than or equal to about 30° to less than or equal to about 40°, greater than or equal to about 40° to less than or equal to about 50°, greater than or equal to about 50° to less than or equal to about 60°, greater than or equal to about 60° to less than or equal to about 70°, or greater than or equal to about 70° to less than or equal to about 80°).

Referring to FIG. 7, the elongated aperture 76 may include a proximal curved portion 168 having a first center 170, a distal curved portion 172 having a second center 174, and a central portion 176. The first center 170 may be disposed at a first distance 178 from the first distal surface 74 in a direction substantially parallel to the longitudinal axis 16. The first and second centers 170, 174 may be disposed a second distance 180 from one another in a direction substantially parallel to the longitudinal axis 16. In certain aspects, the first distance 178 may be less than the second distance 180. In certain aspects, the first distance 178 may be greater than or equal to about 0.25 inch to less than or equal to about 1 inch (e.g., greater than or equal to about 0.25 inch to less than or equal to about 0.5 inch, greater than or equal to about 0.5 inch to less than or equal to about 0.75 inch, or greater than or equal to about 0.75 inch to less than or equal to about 1 inch). The second distance 180 may be greater than or equal to about 0.75 inch to less than or equal to about 2 inches (e.g., greater than or equal to about 0.75 inch to less than or equal to about 1 inch, greater than or equal to about 1 inch to less than or equal to about 1.25 inches, greater than or equal to about 1.25 inches to less than or equal to about 1.5 inches, greater than or equal to about 1.5 inches to less than or equal to about 1.75 inches, or greater than or equal to about 1.75 inches to less than or equal to about 2 inches).

Referring to FIG. 7, the proximal curved portion 168 of the elongated aperture 76 may be substantially semi-circular and define a first diameter 182. The distal curved portion 172 may be substantially semi-circular and define a second diameter 184. The second diameter 184 may be greater than the first diameter 182. In certain aspects, the first diameter 182 may be greater than or equal to about 0.5 inch to less than or equal to about 1 inch (e.g., greater than or equal to about 0.5 inch to less than or equal to about 0.6 inch, greater than or equal to about 0.6 inch to less than or equal to about 0.7 inch, greater than or equal to about 0.7 inch to less than or equal to about 0.8 inch, greater than or equal to about 0.8 inch to less than or equal to about 0.9 inch, or greater than or equal to about 0.9 inch to less than or equal to about 1 inch). The second diameter 184 may be greater than or equal to about 0.5 inch to less than or equal to about 1.5 inches (e.g., greater than or equal to about 0.5 inch to less than or equal to about 0.7 inch, greater than or equal to about 0.7 inch to less than or equal to about 0.9 inch, greater than or equal to about 0.9 inch to less than or equal to about 1.1 inches, greater than or equal to about 1.1 inches to less than or equal to about 1.3 inches, or greater than or equal to about 1.3 inches to less than or equal to about 1.5 inches).

Figure 12:
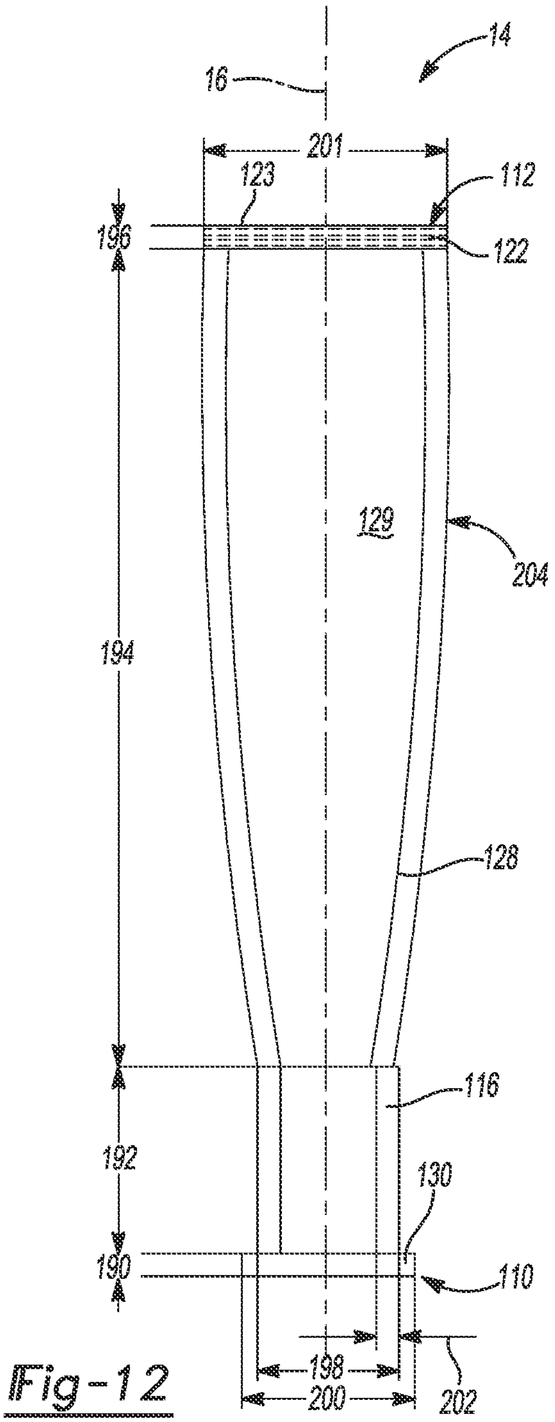
FIG. 12 is another side view of the inner component of FIG. 8.

With Reference to FIG. 12, the plunger 14 includes the second base 116 and the arms 114. The second base 116 defines a fourth height (not shown) substantially parallel to the longitudinal axis 16. The fourth height is a sum of a fifth height 190 of the lip 130 and a sixth height 192 measured between the lip 130 and the arms 114. In certain aspects, the fifth height 190 may be less than the sixth height 192. In certain aspects, the fifth height 190 may be greater than or equal to about 0.05 inch to less than or equal to about 0.1 inch (e.g., greater than or equal to about 0.05 inch to less than or equal to about 0.06 inch, greater than or equal to about 0.06 inch to less than or equal to about 0.07 inch, greater than or equal to about 0.07 inch to less than or equal to about 0.08 inch, greater than or equal to about 0.08 inch to less than or equal to about 0.09 inch, or greater than or equal to about 0.09 inch to less than or equal to about 0.1 inch). The sixth height 192 may be greater than or equal to about 0.5 inch to less than or equal to about 1 inch (e.g., greater than or equal to about 0.5 inch to less than or equal to about 0.6 inch, greater than or equal to about 0.6 inch to less than or equal to about 0.7 inch, greater than or equal to about 0.7 inch to less than or equal to about 0.8 inch, greater than or equal to about 0.8 inch to less than or equal to about 0.9 inch, or greater than or equal to about 0.9 inch to less than or equal to about 1 inch).

The arms 114 define a seventh height (not shown) substantially parallel to the longitudinal axis 16. The seventh height is a sum of an eighth height 194 measured between the second base 116 and the plate 122, and a ninth height 196 of the plate 122. In certain aspects, the eighth height 194 may be greater than the ninth height 196. The eighth height 194 may be greater than or equal to about 2 inches to less than or equal to about 3 inches (e.g., greater than or equal to about 2 inches to less than or equal to about 3 inches, greater than or equal to about 2.25 inches to less than or equal to about 2.5 inches, greater than or equal to about 2.5 inches to less than or equal to about 2.75 inches, or greater than or equal to about 2.75 inches to less than or equal to about 3 inches). The ninth height 196 may be greater than or equal to about 0.05 inch to less than or equal to about 0.25 inch (e.g., greater than or equal to about 0.05 inch to less than or equal to about 0.1 inch, greater than or equal to about 0.1 inch to less than or equal to about 0.15 inch, greater than or equal to about 0.15 inch to less than or equal to about 0.2 inch, or greater than or equal to about 0.2 inch to less than or equal to about 0.25 inch).

The second base 116 defines a seventh dimension 198 (e.g., outer diameter when the second base 116 is cylindrical). The lip 130 defines an eighth dimension 200 (e.g., outer diameter when the lip 130 is cylindrical). The plates 122 define a ninth dimension 201 (e.g., segment length) substantially perpendicular to the fourth dimension 140. In certain aspects, the seventh dimension 198 may be greater than or equal to about 0.25 inch to less than or equal to about 1 inch (e.g., greater than or equal to about 0.25 inch to less than or equal to about 0.5 inch, greater than or equal to about 0.5 inch to less than or equal to about 0.75 inch, or greater than or equal to about 0.75 inch to less than or equal to about 1 inch). The eighth dimension 200 may be greater than or equal to about 0.3 inch to less than or equal to about 1.1 inches (e.g., greater than or equal to about 0.3 inch to less than or equal to about 0.5 inch, greater than or equal to about 0.5 inch to less than or equal to about 0.7 inch, greater than or equal to about 0.7 inch to less than or equal to about 0.9 inch, or greater than or equal to about 0.9 inch to less than or equal to about 1.1 inches). The ninth dimension 201 may be greater than or equal to about 0.5 inch to less than or equal to about 1 inch (e.g., greater than or equal to about 0.5 inch to less than or equal to about 0.6 inch, greater than or equal to about 0.6 inch to less than or equal to about 0.7 inch, greater than or equal to about 0.7 inch to less than or equal to about 0.8 inch, greater than or equal to about 0.8 inch to less than or equal to about 0.9 inch, or greater than or equal to about 0.9 inch to less than or equal to about 1 inch).

The arms 114 and second base 116 define a second thickness 202. In certain aspects, the second thickness 202 may be greater than or equal to about 0.05 inch to less than or equal to about 0.25 inch (e.g., greater than or equal to about 0.05 inch to less than or equal to about 0.1 inch, greater than or equal to about 0.1 inch to less than or equal to about 0.15 inch, greater than or equal to about 0.15 inch to less than or equal to about 0.2 inch, or greater than or equal to about 0.2 inch to less than or equal to about 0.25 inch). In various alternative aspects, the arms 114 and second base 116 may define different thicknesses.

Figure 11:
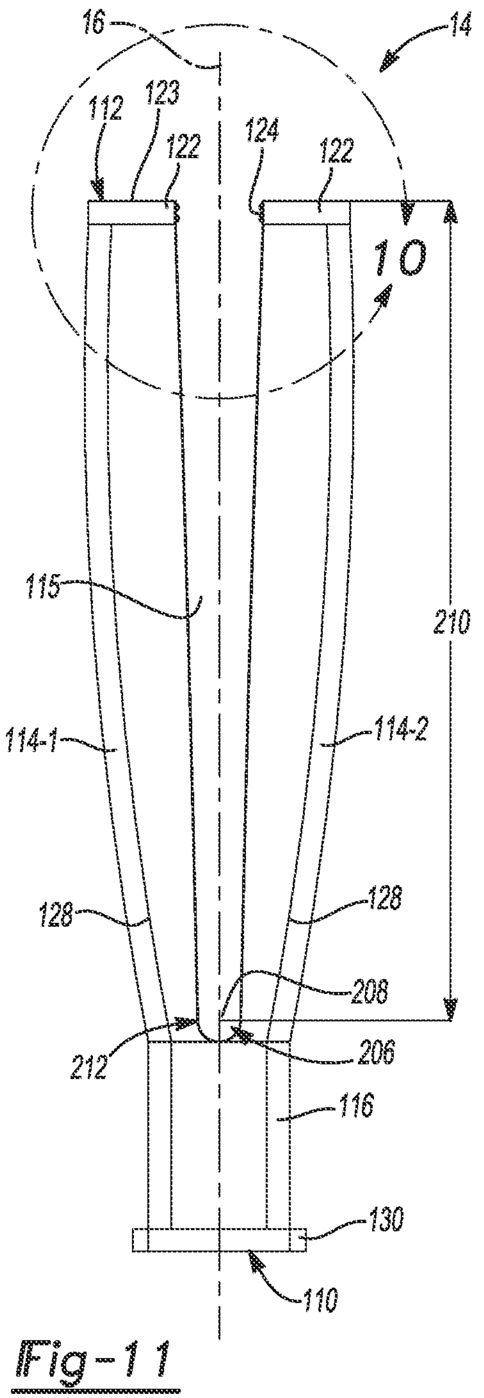
FIG. 11 is a side view of the inner component of FIG. 8.

The outer surfaces 129 of the arms 114 may define a second diameter of curvature 204. In certain aspects, the second diameter of curvature 204 may be greater than or equal to about 5 inches to less than or equal to about 20 inches (e.g., greater than or equal to about 5 inches to less than or equal to about 8 inches, greater than or equal to about 8 inches to less than or equal to about 11 inches, greater than or equal to about 11 inches to less than or equal to about 14 inches, greater than or equal to about 14 inches to less than or equal to about 17 inches, greater than or equal to about 17 inches to less than or equal to about 20 inches). Referring to FIG. 11, the gap 115 may include a third curved portion 206 having a third center 208. The third center 208 may be a third distance 210 from the second distal surface 123 in a direction substantially parallel to the longitudinal axis 16. The third curved portion 206 may have a third diameter 212. In certain aspects, the third distance 210 is greater than or equal to about 1 inch to less than or equal to about 5 inches (e.g., greater than or equal to about 1 inch to less than or equal to about 2 inches, greater than or equal to about 2 inches to less than or equal to about 3 inches, greater than or equal to about 3 inches to less than or equal to about 4 inches, or greater than or equal to about 4 inches to less than or equal to about 5 inches). The third diameter 212 is greater than or equal to about 0.03125 inch to less than or equal to about 0.5 inch (e.g., greater than or equal to about 0.03125 inch to less than or equal to about 0.125 inch, greater than or equal to about 0.125 inch to less than or equal to about 0.25 inch, greater than or equal to about 0.25 inch to less than or equal to about 0.375 inch or greater than or equal to about 0.375 inch to less than or equal to about 0.5 inch).

Figure 9:
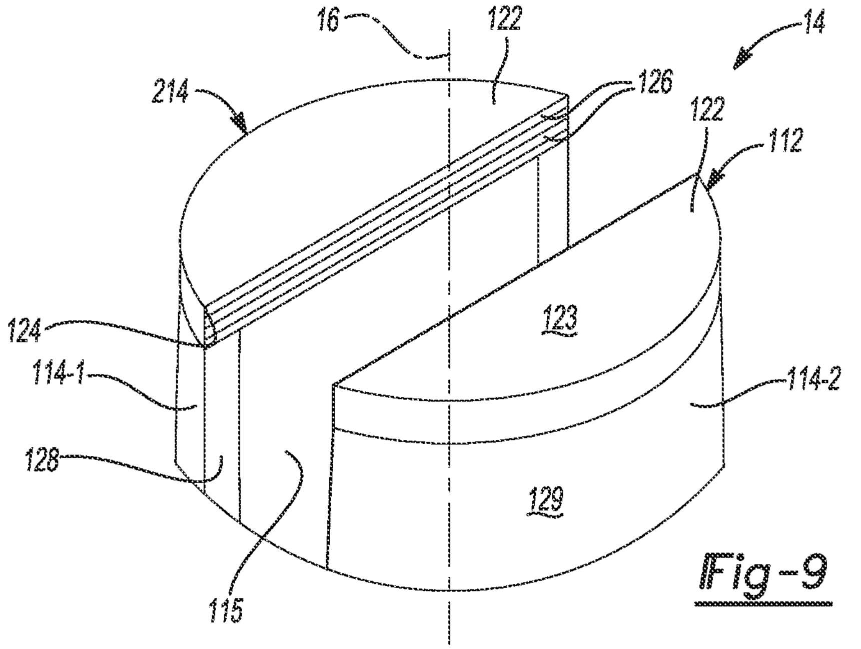
FIG. 9 is a partial perspective detail view of the inner component of FIG. 8.

With reference to FIG. 9, each plate 122 may define a second radius of curvature 214. In certain aspects, the second radius of curvature 214 may be greater than or equal to about 0.1 inch to less than or equal to about 1 inch (e.g., greater than or equal to about 0.1 inch to less than or equal to about 0.2 inch, greater than or equal to about 0.2 inch to less than or equal to about 0.3 inch, greater than or equal to about 0.3 inch to less than or equal to about 0.4 inch, greater than or equal to about 0.4 inch to less than or equal to about 0.5 inch, greater than or equal to about 0.5 inch to less than or equal to about 0.6 inch, greater than or equal to about 0.6 inch to less than or equal to about 0.7 inch, greater than or equal to about 0.7 inch to less than or equal to about 0.8 inch, greater than or equal to about 0.8 inch to less than or equal to about 0.9 inch, greater than or equal to about 0.9 inch to less than or equal to about 1 inch).

Figure 10:
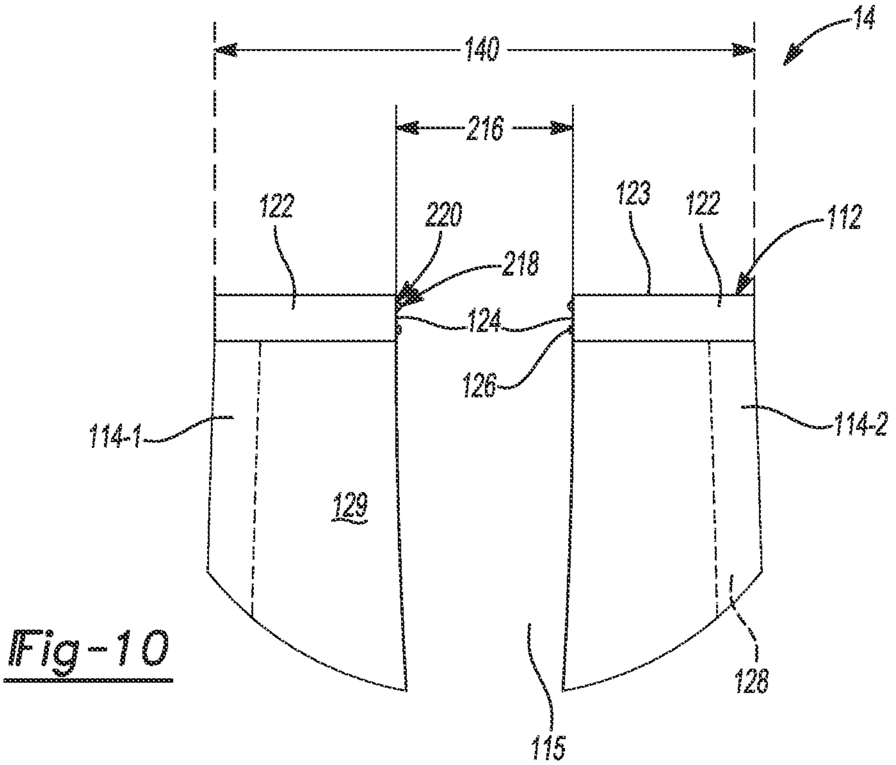
FIG. 10 is a partial side detail view of the inner component of FIG. 8.

Referring to FIG. 10, the grip surfaces 124 may be separated by a fourth distance 216 when the arms 114 are in the open configuration. In certain aspects, the fourth distance 216 may be greater than or equal to about 0.0625 inch to less than or equal to about 1 inch (e.g., greater than or equal to about 0.0625 inch to less than or equal to about 0.125 inch, greater than or equal to about 0.125 inch to less than or equal to about 0.25 inch, greater than or equal to about 0.25 inch to less than or equal to about 0.5 inch, greater than or equal to about 0.5 inch to less than or equal to about 0.75 inch, greater than or equal to about 0.75 inch to less than or equal to about 1 inch).

In certain aspects, each rib 126 may have a substantially semi-cylindrical shape. Each rib 126 may have a fourth diameter 218 of greater than or equal to about 0.01 inch to less than or equal to about 0.1 inch (e.g., greater than or equal to about 0.01 inch to less than or equal to about 0.025 inch, greater than or equal to about 0.025 inch to less than or equal to about 0.05 inch, greater than or equal to about 0.05 inch to less than or equal to about 0.075 inch, or greater than or equal to about 0.075 inch to less than or equal to about 0.1 inch). A third radius of curvature 220 between the each rib 126 and the grip surface 124 may be greater than or equal to about 0.001 inch to less than or equal to about 0.01 inch (e.g., greater than or equal to about 0.001 inch to less than or equal to about 0.0025 inch, greater than or equal to about 0.0025 inch to less than or equal to about 0.005 inch, greater than or equal to about 0.005 inch to less than or equal to about 0.0075 inch, or greater than or equal to about 0.0075 inch to less than or equal to about 0.01 inch).

A fourth distance substantially parallel to the longitudinal axis 16 may be defined between a center of the rib 126 closest the second distal surface 123 and the second distal surface 123. The fourth distance may be greater than or equal to about 0.01 inch to less than or equal to about 0.05 inch (e.g., greater than or equal to about 0.01 inch to less than or equal to about 0.02 inch, greater than or equal to about 0.02 inch to less than or equal to about 0.03 inch, greater than or equal to about 0.03 inch to less than or equal to about 0.04 inch, or greater than or equal to about 0.04 inch to less than or equal to about 0.05 inch). Centers of adjacent ribs 126 may be spaced apart by a fifth distance substantially parallel to the longitudinal axis 16. The fifth distance may be greater than or equal to about 0.01 inch to 0.08 inch (e.g., greater than or equal to about 0.01 inch to less than or equal to about 0.02 inch, greater than or equal to about 0.02 inch to less than or equal to about 0.03 inch, greater than or equal to about 0.03 inch to less than or equal to about 0.04 inch, greater than or equal to about 0.04 inch to less than or equal to about 0.05 inch, greater than or equal to about 0.05 inch to less than or equal to about 0.06 inch, greater than or equal to about 0.06 inch to less than or equal to about 0.07 inch, or greater than or equal to about 0.07 inch to less than or equal to about 0.08 inch).

Example dimensions are depicted in Table 1 below.

TABLE 1

| Dimension | Magnitude |
|---|---|
| First height 150 | 3 inches |
| Third height 152 | 0.5 inch |
| First thickness 154 | 0.0625 inch |
| First dimension 78 | 0.525 inch |
| Second dimension 80 | 1.225 inches |
| Third dimension 82 | 0.525 inch |
| First diameter of curvature 156 | 13.711 inches |
| First length 158 | 1.178 inches |
| Second length 160 | 1.142 inches |
| First angle 60 | 110° |
| Second angle 66 | 55° |
| First radius of curvature 162 | 0.25 inch |
| Sixth dimension 164 | 0.044 inch |
| Third angle 166 | 46° |
| First distance 178 | 0.5 inch |
| Second distance 180 | 1.25 inches |
| First diameter 182 | 0.5 inch |
| Second diameter 184 | 0.75 inch |
| Fifth height 190 | 0.0625 inch |
| Sixth height 192 | 0.55 inch |
| Eighth height 194 | 2.375 inch |
| Ninth height 196 | 0.0625 inch |
| Seventh dimension 198 | 0.4 inches |
| Eighth dimension 200 | 0.5 inch |
| Ninth dimension 201 | 0.71 inch |
| Second thickness 202 | 0.0625 inch |
| Second diameter of curvature 204 | 11.0315 inches |
| Third distance 210 | 2.3125 inches |
| Third diameter 212 | 0.125 inch |
| Second radius of curvature 214 | 0.375 inch |
| Fourth distance 216 | 0.25 inch |
| Fourth diameter 218 | 0.013 inch |
| Third radius of curvature 220 | 0.0016 inch |
| Fourth distance | 0.02 inch |
| Fifth distance | 0.03 inch |

The outer tube 12 and the plunger 14 may each comprise a medical-grade material. In various aspects, the outer tube 12 and the plunger 14 each comprise a medical-grade plastic. Medical-grade plastics may include medical-grade thermoplastics or medical-grade thermosets. Suitable medical-grade thermoplastics may include an acrylonitrile butadiene styrene (ABS), an acetal copolymer (POM-C), an acetal homopolymer (POM-h), a polyethylene terephthalate polyester (PET-P), an ethylene chlorotrifluoroethylene (ECTFE) (e.g., HALAR®), a polybutylene terephthalate-polyester (PBT-P) (e.g., HYDREX®), a polyvinylidene fluoride (PVDF) (e.g., KYNAR®), a polyphenylene oxide (PPO) (e.g., NORYL®), a nylon, a polyetheretherketone (PEEK), a polycarbonate (PC), a thermoplastic polyethylene (PE) (e.g., a high-density thermoplastic polyethylele (HDPE), a low-density polyethylene (LDPE), an ultra-high-molecular-weight polyethylene (UHMWPE)), a polypropylene homopolymer, a polyphenylsulfone (PPSU), a polysulfone (PSU), a polyethersulfone (e.g., RADEL A®), a polyarylethersulfone (e.g., RADEL R®), a polytetrafluoroethylene (PTFE) (e.g., RULON® 641). In certain aspects, the medical-grade plastic may be a modified thermoplastic (e.g., FLUOROSINT®).

With reference to FIGS. 13A-13B, a menstrual cup 310 according to various aspects of the present disclosure is provided. The menstrual cup 310 generally includes a body 312 and a stem 314. The stem 314 can be grasped to remove the menstrual cup 310 from the vagina. The body 312 may be cup-shaped and include an opening 316 to an interior volume 318. The body 312 includes an inner surface 320 in communication with the interior volume 318 and an outer surface 322 opposite the inner surface 320. In certain aspects, the body 312 may include a circumferential lip 324 surrounding the opening 316.

The body 312 may comprise a flexible material (e.g., medical-grade silicone) so that it is collapsible. Accordingly, the menstrual cup 310 can be flexed between an expanded configuration (FIG. 13A) and a collapsed configuration (FIG. 13B). The menstrual cup 310 may be configured to automatically return to the expanded configuration absent an outside force maintaining it in the collapsed position. In the expanded configuration, the circumferential lip 324 may define a substantially circular shape. In certain aspects, in the collapsed configuration, the circumferential lip 324 is deformed into a substantially U-Shape such that it defines an indentation 326.

In various aspects, the present disclosure provides a method of placing the menstrual cup 310 in a vagina using the device 10. The method may include placing the device 10 in the plunged configuration. The device 10 may be placed in the plunged configuration by translating the plunger 14 along the longitudinal axis 16 in the second direction 132 with respect to the outer tube 12.

The method further includes staging the menstrual cup 310 within the device 10. Staging the menstrual cup 310 within the device 10 includes engaging the plunger 14 with the stem 314 of the menstrual cup 310. The user places the stem 314 at least partially within the gap 115. The user pinches the arms 114 from the open configuration toward the longitudinal axis 16 to the closed configuration to engage the stem 314. The user may access the arms 114 through the elongated apertures 76. In the closed configuration, the ribs 126 of the grip surface 124 may engage the stem 314. The body 312 of the menstrual cup 310 may engage the second distal surface 123 of the plunger 14.

Next, while maintaining the plunger 14 in the closed configuration, the user translates the plunger 14 with respect to the outer tube 12 along the longitudinal axis 16 in the first direction 58, from the plunged configuration to the extended configuration. The body 312 of the menstrual cup 310 may engage the chamfer 72 as it slides into the hollow interior region 38 of the outer tube 12. During the translating, the body 312 of the menstrual cup 310 slides along the interior surface 40 and the first sloped surface 56 of the protrusion 44. The engagement with the protrusion 44 causes the menstrual cup 310 to shift from the expanded configuration to the collapsed configuration. During the translating, the arms 114 may engage the second base 116. The engagement may cause the arms 114 to move toward one another and the longitudinal axis, thereby reducing the gap 115.

The method further includes staging the menstrual cup 310 within the vagina. Staging the menstrual cup 310 includes translating the plunger 14 in the second direction 132 along the longitudinal axis 16 with respect to the outer tube 12. The user may grasp the first base 36 of the outer tube 12 and translate the plunger 14 by pressing the second base 116 in the second direction 132. As the body 312 of the menstrual cup 310 becomes disengaged with the protrusion 44, the menstrual cup 310 shifts from the collapsed configuration to the expanded configuration. When the menstrual cup 310 is in the expanded configuration, it has been positioned within the vagina. If applicable, the method further includes removing the device 10 from the vagina. The menstrual cup 310 remains in the vagina in the expanded configuration.

In various aspects, the present disclosure provides a method of removing the menstrual cup 310 from the vagina using the device 10. The method includes placing the device 10 in the plunged configuration. The method further includes engaging the device 10 with the menstrual cup 310. Engaging the device 10 with the menstrual cup 310 may include pinching the stem 314 between the arms 114 of the plunger 14. The user may access the arms 114 through the elongated apertures 76 of the outer tube 12. Because the second distal end 112 of the plunger 14 extends beyond the first distal end 32 of the outer tube 12, the user may access the stem 314 of the menstrual cup by placing the first distal end 32 of the outer tube 12 adjacent to the vagina. In various alternative aspects, the user may insert the first distal end 32 of the outer tube 12 at least partially within the vagina to access the stem 314.

The method further includes transferring the menstrual cup 310 into the device 10. More particularly, while continuing to grasp the stem 314 with the arms 114, the plunger 14 is translated with respect to the outer tube 12 in the first direction 58 along the longitudinal axis 16. The elongated apertures 76 allow the user to maintain contact with the plunger 14 while translating the plunger 14 along the longitudinal axis 16. The body 312 of the menstrual cup 310 engages the protrusion 44 to cause the menstrual cup 310 to transition to the intermediate and/or collapsed configuration, thereby reducing suction holding the device 10 within the vagina. The arms 114 may engage the second base 116 to be forced toward the longitudinal axis 16 and grip the stem 314. Accordingly, in certain aspects, the user may be able to release inward pressure on the stem 314 after beginning translation. After the menstrual cup 310 is removed from the vagina, both the menstrual cup 310 and the device 10 can be cleaned and reused.

Referring to FIG. 14, another device 410 for placement and removal of a menstrual cup (e.g., menstrual cup 310 of FIGS. 13A-13B) according to various aspects of the present disclosure is provided. The device 410 includes an outer component or outer tube 412 and an inner component or plunger 414. At least one of the outer tube 412 and the plunger 414 is translatable along a longitudinal axis 416 with respect to the other of the outer tube 412 and the plunger 414. The device 410 is therefore movable between a plunged configuration (FIGS. 14, 21) and an extended configuration (FIG. 22). As will be discussed in greater detail below (see discussion accompanying FIGS. 24-26), the device 410 may be used for placement of the menstrual cup in a vagina and/or removal of the menstrual cup from the vagina.

The outer tube 412 extends between a first proximal end 418 and a first distal end 420. The outer tube 412 includes a peripheral wall 422 that extends between the first proximal end 418 and the first distal end 420. The outer component further includes a first hollow interior region 424 that is at least partially defined by the peripheral wall 422.

In certain aspects, the outer tube 412 may include a first or upper portion 430 and a second or lower portion 432. Accordingly, the upper and lower portions 430, 432 cooperate to form the outer tube 412. The upper and lower portions 430, 432 are separable from one another. The outer tube 412 is movable between a coupled configuration, as shown in FIG. 14, and a decoupled configuration in which the upper and lower portions 430, 432 are decoupled (see upper portion 430 of FIGS. 15-16 and lower portion 432 of FIGS. 17-18).

Figure 15:
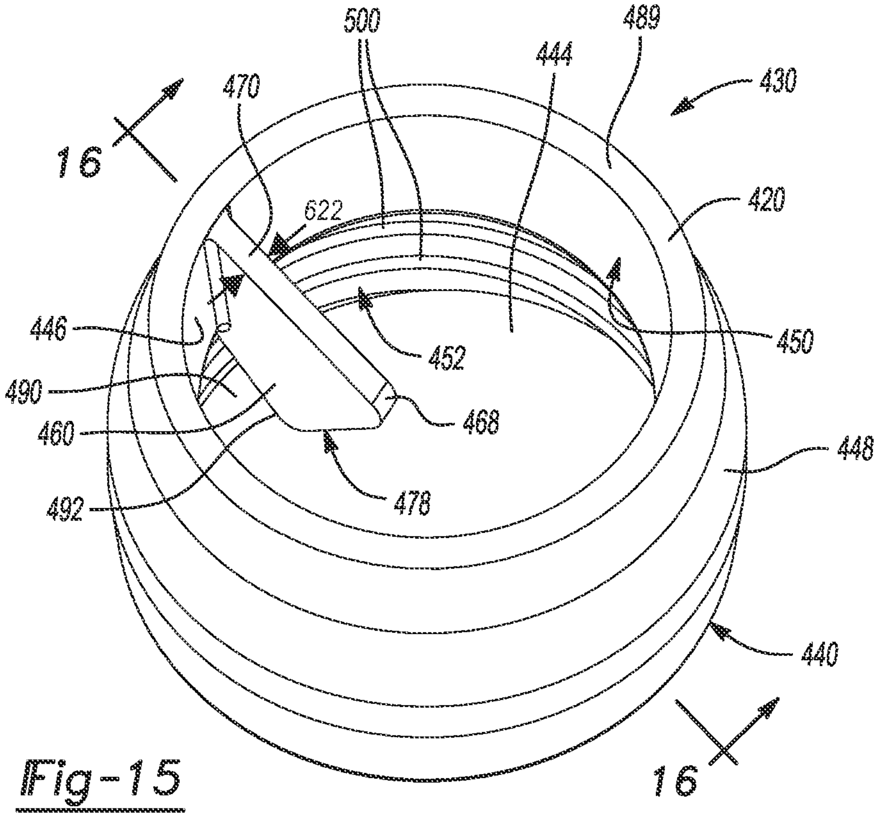
FIG. 15 is a perspective view of an upper portion of an outer component of the device of FIG. 14.
Figure 16:
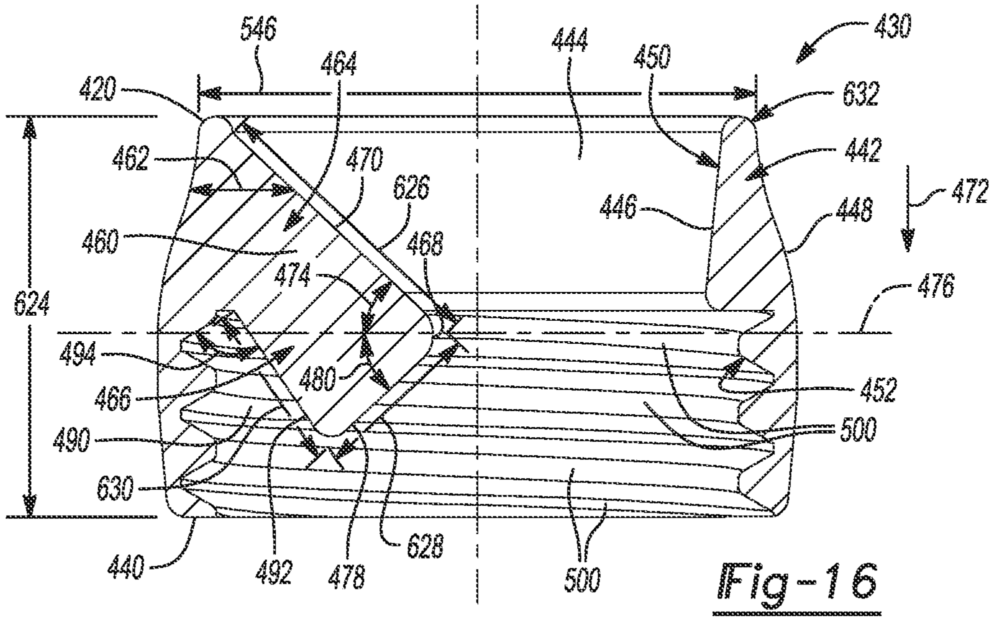
FIG. 16 is a sectional view of the upper portion of FIG. 15 taken at line 16-16 of FIG. 15.

With reference to FIGS. 15-16, the upper portion 430 of the outer tube 412 is provided. The upper portion 430 extends between the first distal end 420 and a first intermediate end 440 (intermediate with respect to the outer tube 412). The upper portion 430 includes a first or upper peripheral wall portion 442 that at least partially defines an upper interior region 444. The upper interior region 444 is configured to receive at least a portion of a menstrual cup.

The upper portion 430 includes a first interior surface 446 and a first exterior surface 448. The first interior surface 446 is disposed closer to the longitudinal axis 416 and is in communication with the upper interior region 444. The first interior surface 446 includes a cup engagement portion 450 and a lower engagement portion 452.

The upper portion 430 may include a protrusion 460 that extends into the upper interior region 444. The protrusion 460 may extend from the cup engagement portion 450 of the first interior surface 446. In certain aspects, the protrusion 460 may be integrally formed with the upper peripheral wall portion 442. The protrusion 460 may be immovable with respect to the upper peripheral wall portion 442. The upper portion 430 may be a single-piece, unitary structure.

The protrusion 460 may be configured to engage the menstrual cup. More particularly, when the menstrual cup is pulled into the upper portion 430, the protrusion 460 engages the menstrual cup to at least partially collapse the menstrual cup so that the menstrual cup is in an intermediate configuration (see, e.g., FIG. 25D) or a collapsed configuration (see, e.g., FIGS. 25A-25C). When the menstrual cup is ejected from the device 410, the menstrual cup may progressively disengage the protrusion 460 to shift into the expanded configuration (see, e.g., FIG. 25E).

In certain aspects, the protrusion 460 may be sized and shaped to gradually collapse and/or expand the menstrual cup. For example, as shown in FIG. 16, the protrusion 460 may include a radial dimension 462 measured between the upper peripheral wall portion 442 and the longitudinal axis 416 that varies along the longitudinal axis 416. The protrusion 460 may include a first or upper protrusion portion 464, a second or lower protrusion portion 466, and an apex 468 disposed between the first and second portions 464, 466.

The first portion 464 includes a first sloped surface 470. In the first portion 464 of the protrusion 460, the radial dimension 462 may increase in a first direction 472 defined by a vector extending substantially parallel to the longitudinal axis 416 from the first distal end 420 to the first intermediate end 440. The first portion 464 may extend from adjacent to the first distal end 420 to the apex 468.

The first portion 464 may be configured to slidingly engage the menstrual cup. The first sloped surface 470 may form a first angle 474 with a plane 476 that extends substantially perpendicular to the longitudinal axis 416. The first angle 474 may be greater than or equal to about 20° to less than or equal to about 75° (e.g., greater than or equal to about 20° to less than or equal to about 25°, greater than or equal to about 25° to less than or equal to about 30°, greater than or equal to about 30° to less than or equal to about 35°, greater than or equal to about 35° to less than or equal to about 40°, greater than or equal to about 40° to less than or equal to about 45°, greater than or equal to about 45° to less than or equal to about 50°, greater than or equal to about 50° to less than or equal to about 55°, greater than or equal to about 55° to less than or equal to about 60°, greater than or equal to about 60° to less than or equal to about 65°, or greater than or equal to about 65° to less than or equal to about 70°). In certain aspects, the first angle 474 may be greater than or equal to about 20° to less than or equal to about 65°, or optionally greater than or equal to about 35° to 55°. In certain aspects, the first angle 474 may be about 45°. In certain alternative aspects, the first angle 474 may be about 60°.

In various aspects, the second portion 466 of the protrusion 460 includes a second sloped surface 478. The first and second sloped surface 470, 478 may cooperate to define a substantially V-shape. In the second portion 466, the radial dimension 462 of the protrusion 460 may decrease in the first direction 472. The second sloped surface 478 may form a second angle 480 with the plane 476. In some examples, the second angle 480 may be greater than or equal to about 20° to less than or equal to about 65° (e.g., greater than or equal to about 20° to less than or equal to about 25°, greater than or equal to about 25° to less than or equal to about 30°, greater than or equal to about 30° to less than or equal to about 35°, greater than or equal to about 35° to less than or equal to about 40°, greater than or equal to about 40° to less than or equal to about 45°, greater than or equal to about 45° to less than or equal to about 50°, greater than or equal to about 50° to less than or equal to about 55°, greater than or equal to about 55° to less than or equal to about 60°, greater than or equal to about 60° to less than or equal to about 65°). In certain aspects, the second angle 480 may be about 45°. In certain alternative aspects, the second angle 480 may be about 60°. In certain aspects, the second angle 480 may be substantially the same as the first angle 474. In various aspects, the second sloped surface 478 and rounded shape of the apex 468 may facilitate removal of the menstrual cup from the upper portion 430 without substantially inhibiting translation of the menstrual cup along the longitudinal axis 416.

The second portion 466 of the protrusion 460 may define an undercut 490. The undercut 490 may provide clearance for the lower portion 432 (FIG. 14) when the outer tube 412 is in the coupled configuration. The undercut 490 may include a third sloped surface 492. The third sloped surface 492 may define a third angle 494 with respect to the plane 476. In certain aspects, the third angle 494 may be greater than or equal to about 100° to less than or equal to about 170°. In some examples, the third angle 494 may be greater than or equal to about 110° to less than or equal to about 160°, optionally greater than or equal to about 115° to less than or equal to about 135°, optionally greater than or equal to about 120° to less than or equal to about 130°, or optionally about 125°.

As discussed above, the protrusion 460 may extend toward the longitudinal axis 416. In certain aspects, the apex 468 of the protrusion 460 may extend greater than or equal to about 10%, optionally greater than or equal to about 20%, optionally greater than or equal to about 30%, optionally greater than or equal to about 40%, optionally greater than or equal to about 50%, optionally greater than or equal to about 60%, optionally greater than or equal to about 70%, or optionally greater than or equal to about 80% of a distance between the first interior surface 446 (at the same longitudinal location) and the longitudinal axis 416.

The cup engagement portion 450 of the first interior surface 446 is configured to engage the menstrual cup as the menstrual cup slides in and out of the upper portion 430. In certain aspects, the cup engagement portion 450 may be smooth, as shown. In certain alternative aspects, the cup engagement portion 450 may define a plurality of indentations or projections to reduce a contact area of the cup engagement portion 450 that will engage the menstrual cup and therefore facilitate sliding of the menstrual cup with respect to the upper portion 430. The indentations or projections may be similar to those described above in the discussion accompanying FIGS. 6-7 (see, e.g., indentations 70).

The first distal end 420 includes a first distal surface 498. The first distal surface 498 may be rounded between the first interior and exterior surfaces 446, 448 to facilitate transition of the menstrual cup into and out of the upper portion 430 and/or increase comfort of the user during insertion of the device 410 into the vagina. Additionally or alternatively, the first distal end 420 may include one or more chamfers (see, e.g., chamfer 72 of FIG. 7).

The lower engagement portion 452 of the first interior surface 446 may define a first plurality of threads 500 for engagement with the lower portion 432 (FIG. 14). The lower engagement portion 452 may additionally or alternatively include other mechanical engagement features for coupling the upper portion 430 to the lower portion 432. Other features may include twist lock, snap fit, interlock, protrusion (e.g., hook, bread, stud, and/or bump), by way of example.

Figure 17:
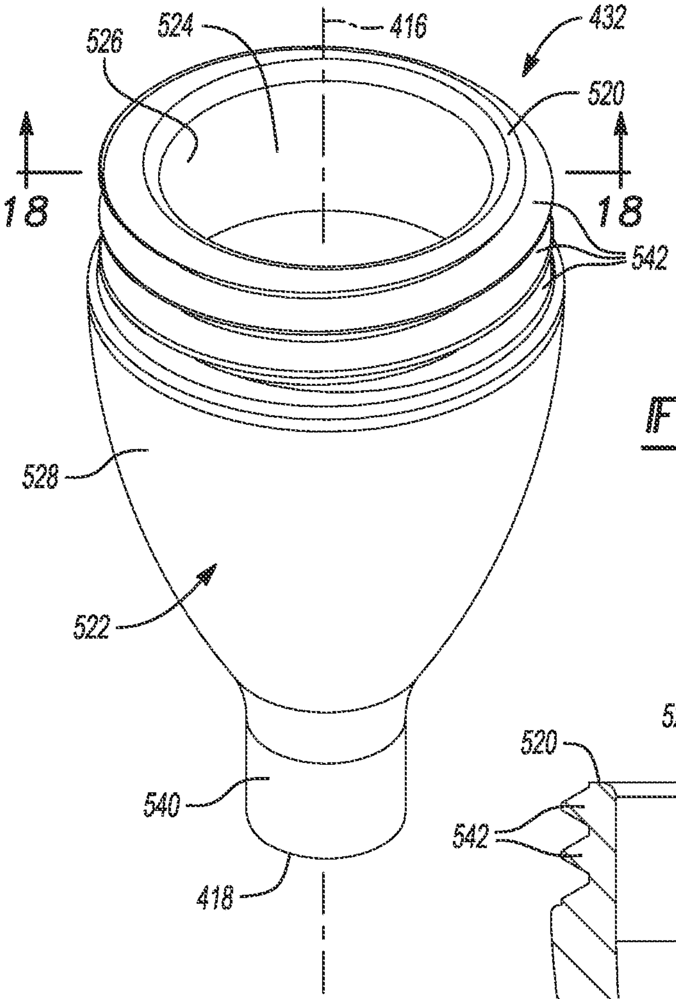
FIG. 17 is a perspective view of a lower portion of the outer component of the device of FIG. 14.
Figure 18:
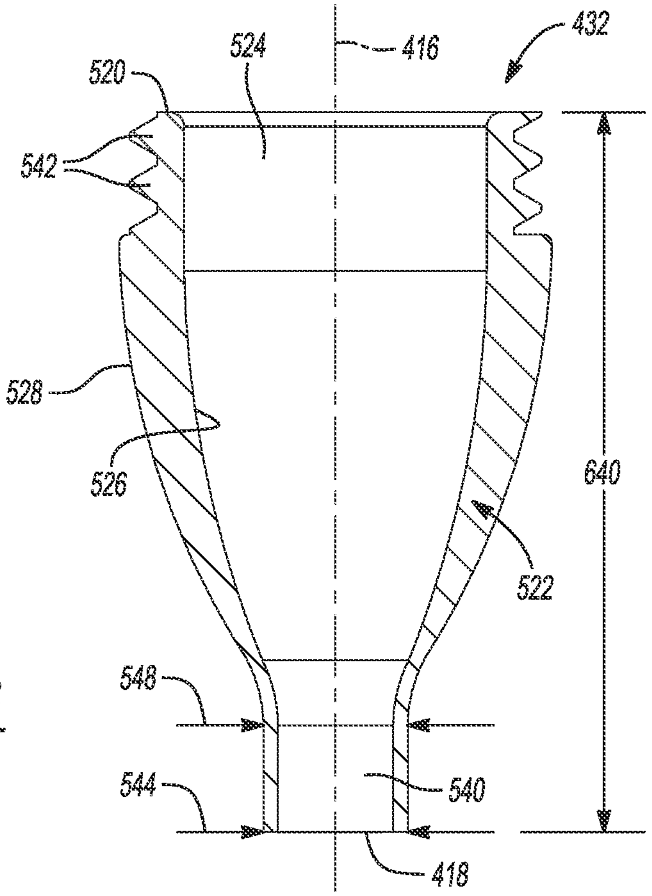
FIG. 18 is a sectional view of the lower portion of FIG. 17, taken at line 18-18 of FIG. 17.

Referring to FIGS. 17-18, the lower portion 432 of the outer tube 412 is provided. The lower portion 432 extends between a second intermediate end 520 and the first proximal end 418. The lower portion 432 includes a second or lower peripheral wall portion 522 that at least partially defines a lower interior region 524. The lower peripheral wall portion 522 cooperates with the upper peripheral wall portion 442 of the upper portion 430 to form the peripheral wall 422 of the outer tube 412. The lower interior region 524 cooperates with the upper interior region 444 to form the first hollow interior region 424 of the outer tube 412.

The lower portion 432 further includes a second interior surface 526 and a second exterior surface 528. The second interior surface 526 is disposed closer to the longitudinal axis 416 than the second exterior surface 528. The second interior surface 526 is in communication with the lower interior region 524.

The lower portion 432 of the outer tube 412 further includes a first base 540. The first base 540 may include the first proximal end 418. During placement of the menstrual cup, the user may grip the lower portion 432 of the outer tube 412 at the first base 540. The first base 540 may have a substantially smooth surface. In various alternative aspects, the first base may include a gripping feature such as one or more indentations and/or one or more projections, as described above in the discussion accompanying FIGS. 6-7 (see, e.g., projections 84). Additionally or alternatively, other portions of the first and/or second exterior surfaces 448, 528 may include gripping features.

The lower portion 432 further includes a second plurality of threads 542. The threads 542 are disposed adjacent to the second intermediate end 520 of the lower portion 432. The threads 542 of the lower portion 432 are shaped and sized to engage the threads 500 of the upper portion 430 to removably couple the upper portion 430 to the lower portion 432.

Although the threads 500, 542 are shown on the first interior and second exterior surfaces 446, 528 respectively, they may alternatively be disposed on the first exterior and second interior surfaces 448, 526 respectively.

As used herein, "removably couple" means that the upper and lower portions 430, 432 may be repeated coupled and decoupled without substantial damage to the outer tube 412. Moreover, in certain aspects, the upper and lower portions 430, 432 may be readily coupled and decoupled on-to-go without the use of additional tools or equipment. As noted above with respect to the upper portion 430, the lower portion 432 may additionally or alternatively include other coupling features, such as twist lock, snap fit, interlock, protrusion (e.g., hook, bread, stud, and/or bump), by way of example.

Returning to FIG. 14, the upper and lower portions 430, 432 cooperate to form the outer tube 412. The outer tube 412 may define a substantially circular cross section. A diameter of the substantially circular cross section may vary along the longitudinal axis 416. The first proximal end 418 defines a first dimension 544 (FIG. 18). The first distal end 420 defines a second dimension 546 (FIG. 16) that may be larger than the first dimension 544. The first base 540 may be substantially cylindrical such that a third dimension 548 (FIG. 18) adjacent to the first base 540 is substantially the same as the first dimension 544. However, in various alternative aspects, the first base 540 may be non-cylindrical. In certain aspects, the peripheral wall 422 may define a portion of an elliptic paraboloid shape, with the second dimension 546 being greater than the third dimension 548.

In various alternative aspects, the peripheral wall 422 and first base 540 may define other shapes. In one example, the peripheral wall 422 is substantially frusto-conical. In another example, the peripheral wall 422 is substantially cylindrical (not shown). In yet other examples, one or both of the peripheral wall 422 and the first base 540 have non-circular cross sections (e.g., substantially triangular, square, pentagonal, hexagonal, heptagonal, octagonal, nonagonal, or decagonal). Although interior surface 446, 526 and the exterior surfaces 448, 528 are shown as having substantially the same cross-sectional shapes with respect to the longitudinal axis 416 (i.e., circular), they may alternatively define different cross-sectional shapes. In one example, the interior surfaces 446, 526 define substantially octagonal cross sections, and the exterior surfaces 448, 528 define substantially circular cross section.

Figure 19:
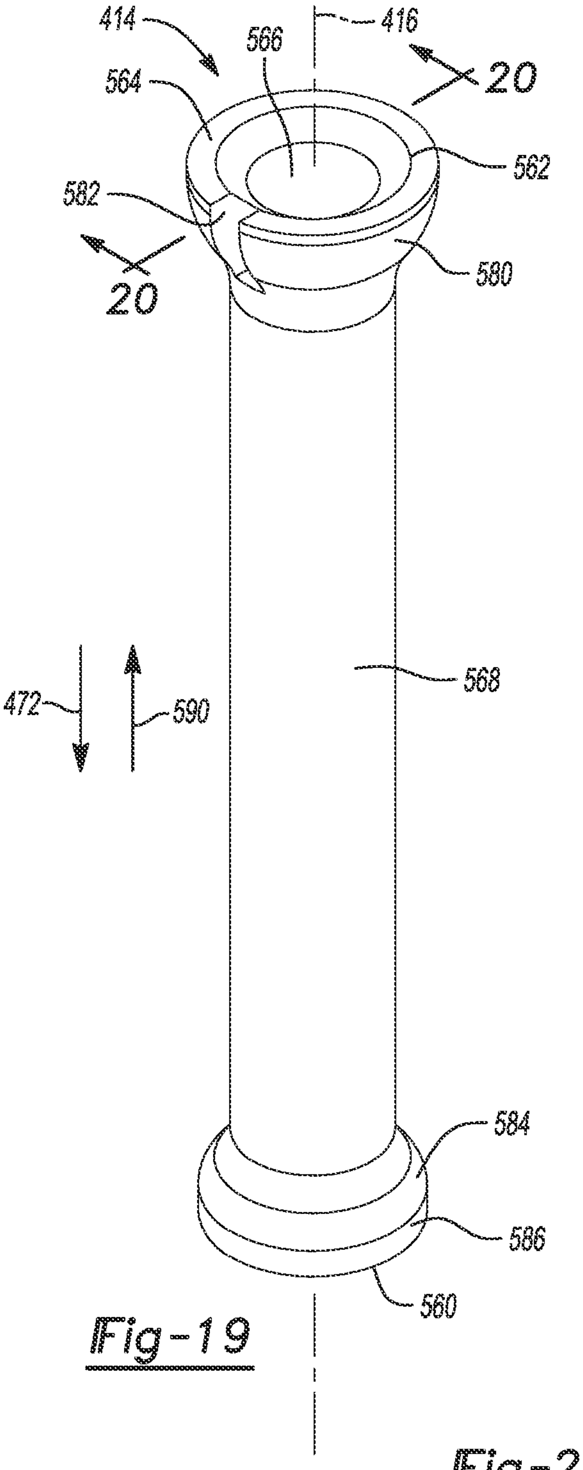
FIG. 19 is a perspective view of an inner component of the device of FIG. 14.
Figure 20:
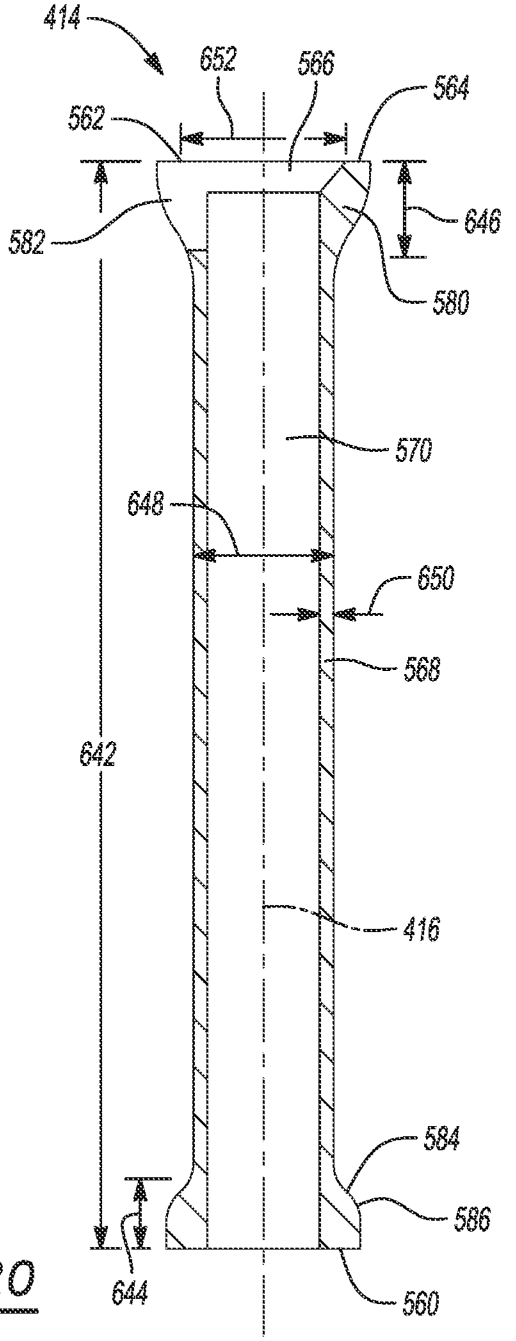
FIG. 20 is a sectional view of the inner component of FIG. 19, taken at line 20-20 of FIG. 19.

Referring to FIGS. 19-20, the plunger 414 according to various aspects of the present disclosure is provided. The plunger 414 extends along the longitudinal axis 416 between a second proximal end 560 and a second distal end 562. In certain aspects, the plunger 414 may be a single-piece, unitary structure. In certain aspects, the plunger 414 may be substantially rigid such it is free of movable portions.

The second distal end 562 includes a second distal surface 564. In certain aspects, the second distal surface 564 may be substantially planar. The second distal surface 564 defines an aperture 566. The aperture 566 may accommodate a stem of the menstrual cup when the menstrual cup is disposed within the device 410 (FIG. 14). In various aspects, the second distal surface 564 may be substantially ring-shaped.

In certain aspects, the plunger 414 may be hollow. Accordingly, the plunger 414 may include a plunger wall 568 defining a second hollow interior region 570 (FIG. 20). The second hollow interior region 570 may be in fluid communication with the aperture 566. In various alternative aspects, the plunger 414 may substantially solid or partially hollow. In certain aspects, the plunger wall 568 may be hollow cylindrical and uninterrupted such that it is free of movable portions (e.g., arms).

The second distal end 562 may be flared radially outwardly to define a first flange 580. The second distal end 562 may define a notch 582. In certain aspects, the notch 582 may be at least partially defined by the first flange 580.

The plunger 414 may include a second base 584 disposed adjacent to the second proximal end 560. In certain aspects, the second proximal end 560 may be flared radially outwardly in a second flange 586 to define the second base 584. In various alternative aspects, the second base 584 may define a lip (see, e.g., lip 130 of FIG. 8).

Figure 21:
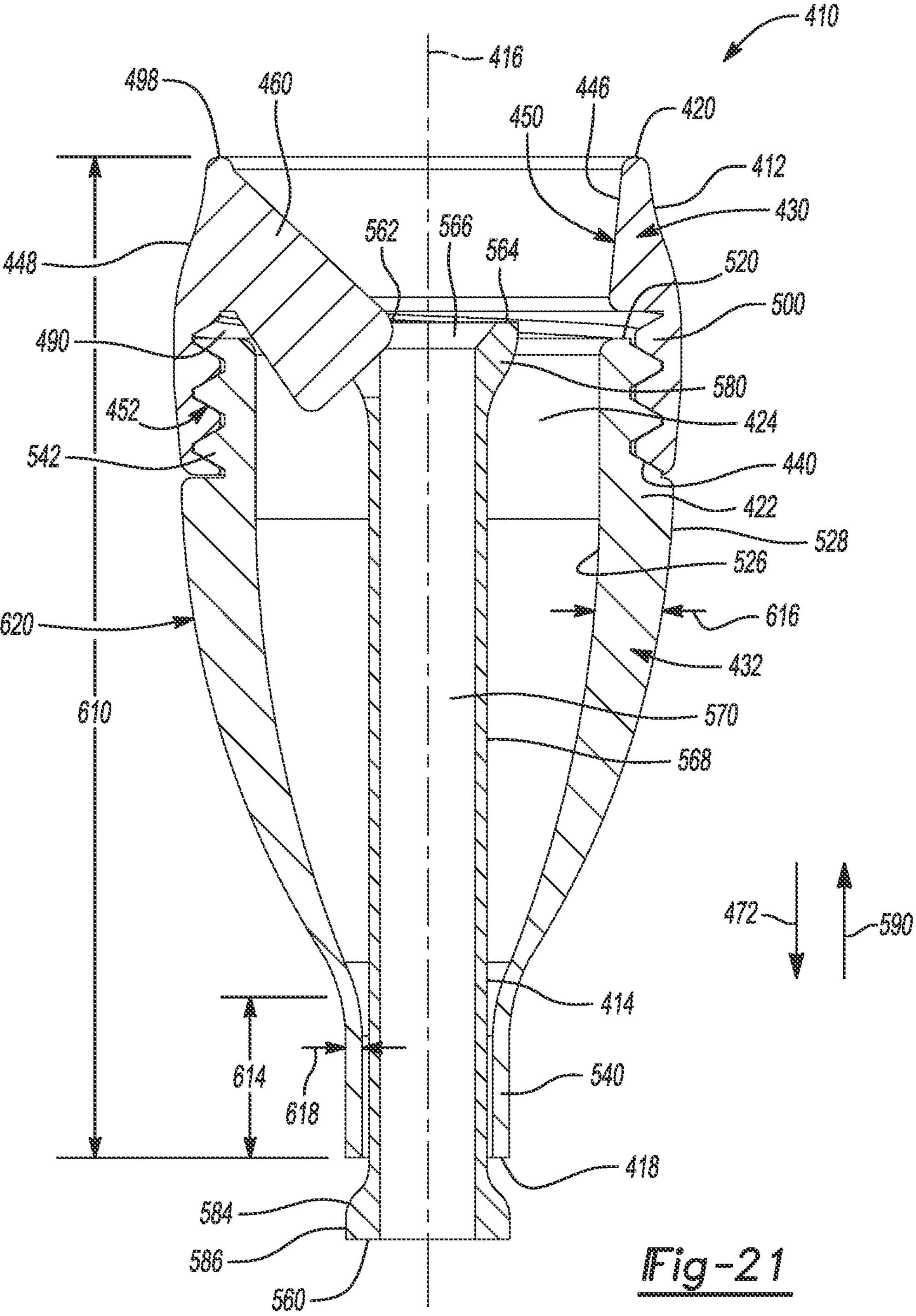
FIG. 21 is a sectional view of the device of FIG. 14, the device being in the plunged configuration.
Figure 22:
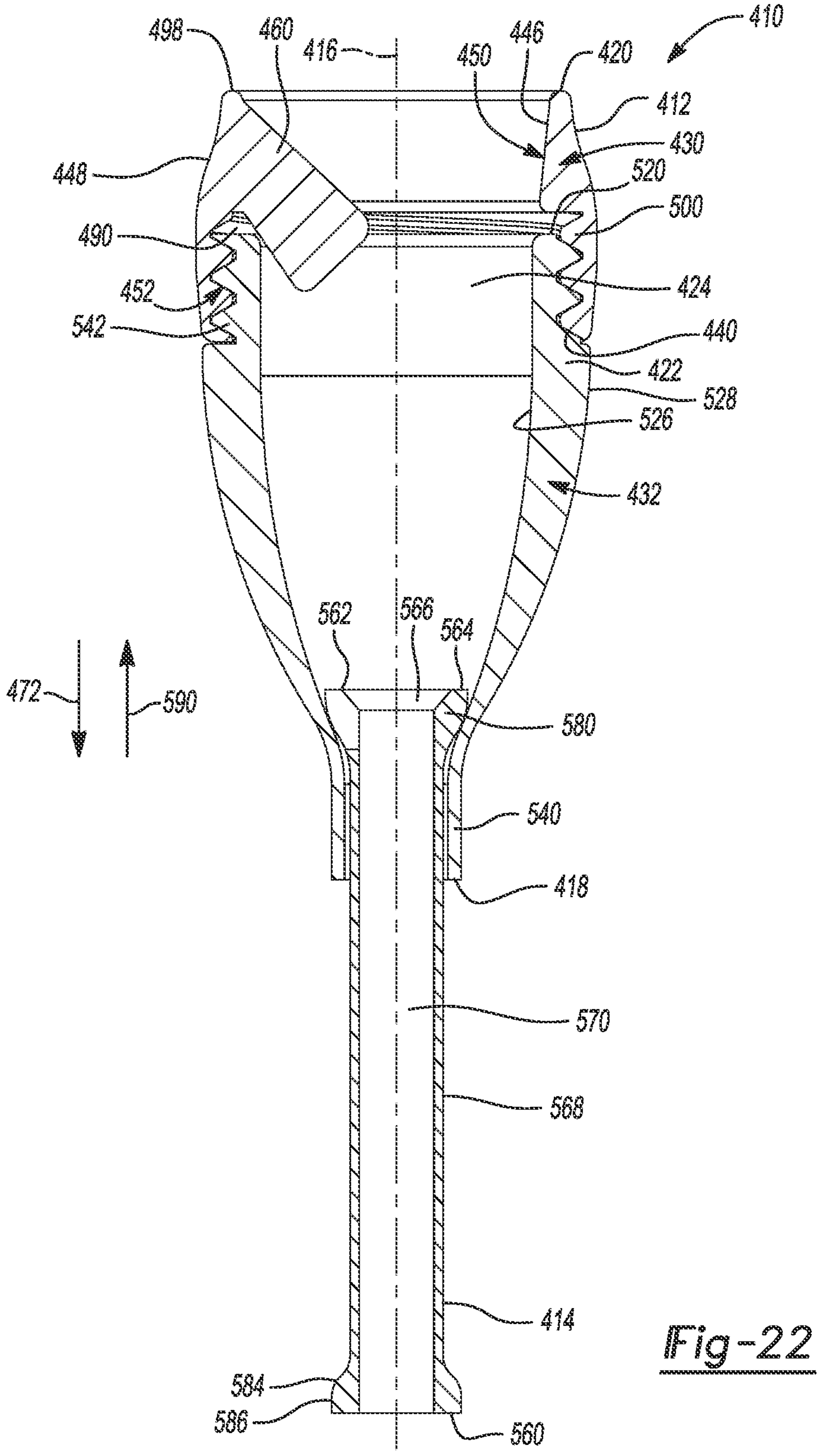
FIG. 22 is a sectional view of the device of FIG. 14, the device being in an extended configuration.
Figure 23:
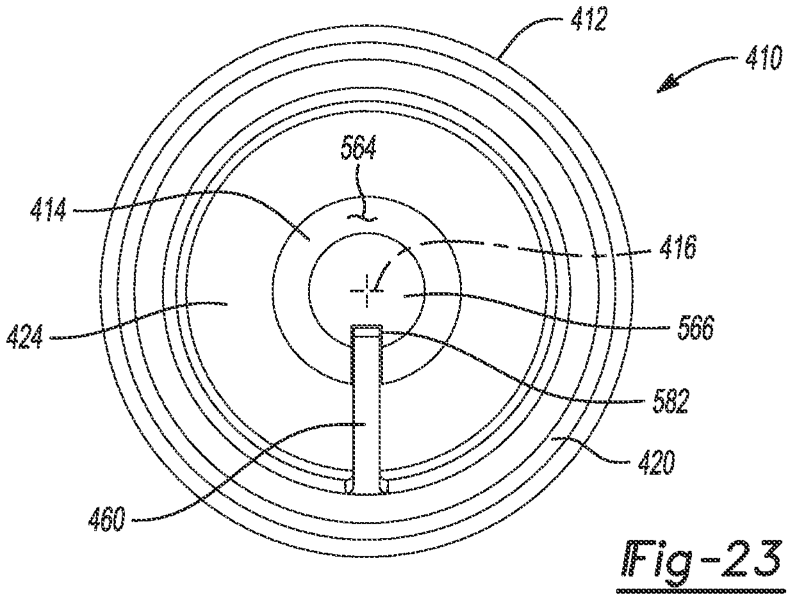
FIG. 23 is a top view of the device of FIG. 14.

Referring to FIGS. 21-23, the device 410 is provided. The upper and lower portions 430, 432 of the outer tube 412 are coupled to one another. More particularly, the first and second pluralities of threads 500, 542 are engaged to couple the upper portion 430 to the lower portion 432. The second intermediate end 520 of the lower portion 432 is at least partially disposed within the undercut 490 of the protrusion 460.

The plunger 414 is disposed at least partially within the first hollow interior region 424. The outer tube 412 and the plunger 414 are substantially aligned along the longitudinal axis 416. When the device 410 is in the plunged configuration, the protrusion 460 is at least partially disposed within the notch 582 of the plunger 414.

The outer tube 412 and the plunger 414 are slidable with respect to one another along the longitudinal axis 416 between the plunged configuration (FIG. 21) and the extended configuration (FIG. 22). For example, the plunger 414 may be translated in the first direction 472 with respect to the outer tube 412 to move the device 410 from the plunged configuration to the extended configuration. The plunger 414 may be translated in a second direction 590 opposite the first direction 472 with respect to the outer tube 412 to move the device 410 from the extended configuration to the plunged configuration.

In certain aspects, the first and second flanges 580, 586 may facilitate retention of the plunger 414 within the lower portion 432 of the outer tube 412. The first flange 580 may engage the lower peripheral wall portion 522 and/or the first base 540 to prevent translation of the plunger 414 past a first predetermined location on the longitudinal axis 416 (e.g., the first base 540) in the first direction 472. The second flange 586 may engage the first base 540 to prevent translation of the plunger 414 past a second predetermined location along the longitudinal axis (e.g., the first base 540) in the second direction 590. In certain aspects, in the plunged configuration, the second distal end 562 of the plunger 414 may be substantially flush with the second intermediate end 520 of the lower portion 432. However, in various alternative aspects, the second distal end 562 may project or be recessed with respect to the second intermediate end 520.

The device 410 may define various sizes and shapes. The device may generally define similar dimensions as the device 10 of FIGS. 1-12. Example dimensions are described below. However, one skilled in the art will appreciate that devices according to various aspects of the present disclosure may have different dimensions, shapes, and configurations, depending at least on size and style of the menstrual cup.

As shown in FIG. 21, the outer tube 412 may define a first height 610 substantially perpendicular to the longitudinal axis 416. The first height 610 is a sum of a second height (not shown) of the peripheral wall 422 and a third height 614 of the first base 540. In certain aspects, the first height 610 may be greater than or equal to about 2 inches to less than or equal to about 5 inches. The third height 614 may be greater than or equal to about 0.5 inch to less than or equal to about 1.5 inches (e.g., greater than or equal to about 0.5 inch to less than or equal to about 0.75 inch, greater than or equal to about 0.75 inch to less than or equal to about 1.0 inch, greater than or equal to about 1.0 inch to less than or equal to about 1.25 inches, or greater than or equal to about 1.25 inches to less than or equal to about 1.5 inches).

The peripheral wall 422 may define a first thickness 616. The first thickness 616 may be variable along the longitudinal axis 416. In certain aspects, the first thickness 161 may vary between greater than or equal to about 0.0625 inches and less than or equal to about 0.5 inches, or optionally about 0.225 inches. The first base 540 may define a second thickness 618. In certain aspects, the second thickness 618 may be substantially uniform. For example, the second thickness 618 may be greater than or equal to about 0.01 inches to less than or equal to about 0.5 inches.

The first and second exterior surfaces 448, 528 of the peripheral wall 422 may cooperate to define a first diameter of curvature 620. In certain aspects, the first diameter of curvature 620 may be greater than or equal to about 2 inches to less than or equal to about 10 inches (e.g., greater than or equal to about 2 inches to less than or equal to about 3 inches, greater than or equal to about 3 inches to less than or equal to about 4 inches, greater than or equal to about 4 inches to less than or equal to about 5 inches, greater than or equal to about 5 inches to less than or equal to about 6 inches, greater than or equal to about 6 inches to less than or equal to about 7 inches, greater than or equal to about 7 inches to less than or equal to about 8 inches, greater than or equal to about 8 inches to less than or equal to about 9 inches, or greater than or equal to about 9 inches to less than or equal to about 10 inches).

With reference to FIG. 23, in certain aspects, the protrusion 460 may define a third thickness 622 of greater than or equal to about 0.01 inches to less than or equal to about 0.5 inches. For example, the third thickness 622 may be greater than or equal to about 0.01 inches to less than or equal to about 0.1 inches, greater than or equal to about 0.1 inches to less than or equal to about 0.25 inches, greater than or equal to about 0.25 inches to less than or equal to about 0.5 inches.

As described above, the outer tube 412 may have the first dimension 544 (FIG. 18), the second dimension 546 (FIG. 16), and the third dimension 548 (FIG. 18). In certain aspects, the first dimension 544 may be greater than or equal to about 0.25 inch to less than or equal to about 1 inch (e.g., greater than or equal to about 0.25 inch to less than or equal to about 0.5 inch, greater than or equal to about 0.5 inch to less than or equal to about 0.75 inch, greater than or equal to about 0.75 inch to less than or equal to about 1 inch). The second dimension 546 may be greater than or equal to about 0.75 inch to less than or equal to about 1.5 inches (e.g., greater than or equal to about 0.75 inch to less than or equal to about 1 inch, greater than or equal to about 1 inch to less than or equal to about 1.25 inches, greater than or equal to about 1.25 inches to less than or equal to about 1.5 inches). The third dimension 548 may be greater than or equal to about 0.75 inch to less than or equal to about 1.5 inches (e.g., greater than or equal to about 0.75 inch to less than or equal to about 1 inch, greater than or equal to about 1 inch to less than or equal to about 1.25 inches, greater than or equal to about 1.25 inches to less than or equal to about 1.5 inches).

Returning to FIG. 16, the upper portion 430 of the outer tube 412 may define a fourth height 624. In certain aspects, the fourth height 624 may be greater than or equal to about 0.25 inches to less than or equal to about 3 inches. For example, the fourth height 624 may be greater than or equal to about 0.25 inches to less than or equal to about 0.5 inches, greater than or equal to about 0.5 inches to less than or equal to about 1 inch, greater than or equal to about 1 inch to less than or equal to about 2 inches, or greater than or equal to about 2 inches to less than or equal to about 3 inches.

The first sloped surface 470 of the protrusion 460 may define a first length 626. In certain aspects, the first length 626 may be greater than or equal to about 0.25 inches to less than or equal to about 1.5 inches. For example, the first length 626 may be greater than or equal to about 0.25 inches to less than or equal to about 0.5 inches, greater than or equal to about 0.5 inches to less than or equal to about 0.75 inches, greater than or equal to about 0.75 inches to less than or equal to about 1 inch, greater than or equal to about 1 inch to less than or equal to about 1.5 inches.

The second sloped surface 478 of the protrusion 460 may define a second length 628. In certain aspects, the second length 628 may be greater than or equal to about 0.125 inches to less than or equal to about 1.25 inches. For example, the second length 628 may be greater than or equal to about 0.125 inches to less than or equal to about 0.25 inches, greater than or equal to about 0.25 inches to less than or equal to about 0.5 inches, greater than or equal to about 0.5 inches to less than or equal to about 0.75 inches, greater than or equal to about 0.75 inches to less than or equal to about 1 inch, or greater than or equal to about 1 inch to less than or equal to about 1.5 inches.

The third sloped surface 492 of the protrusion 460 may define a third length 630. In certain aspects, the third length 630 may be greater than or equal to about 0.0625 inches to less than or equal to about 1.5 inches. For example, the third length 630 may be greater than or equal to about 0.0625 inches to less than or equal to about 0.125 inches, greater than or equal to about 0.125 inches to less than or equal to about 0.25 inches, greater than or equal to about 0.25 inches to less than or equal to about 0.5 inches, greater than or equal to about 0.5 inches to less than or equal to about 1 inch, greater than or equal to about 1 inch to less than or equal to about 1.5 inches.

The first distal surface 498 may define a second radius of curvature 632. In certain aspects, the second radius of curvature 632 may be greater than or equal to about 0.0125 inches to less than or equal to about 0.25 inches.

Referring to FIG. 18, the lower portion 432 of the outer tube 412 may define a fifth height 640. In certain aspects, the fifth height 640 may be greater than or equal to about 0.75 inches to less than or equal to about 4 inches. For example, the fifth height 640 may be greater than or equal to about 0.75 inches to less than or equal to about 1.25 inches, greater than or equal to about 1.25 inches to less than or equal to about 2 inches, greater than or equal to about 2 inches to less than or equal to about 3 inches, or greater than or equal to about 3 inches to less than or equal to about 4 inches.

With reference to FIG. 20, the plunger 414 defines a sixth height 642, the second flange 586 defines a seventh height 644, and the first flange 580 defines an eighth height 646. The sixth height 642 may be greater than or equal to about 1 inch to less than or equal to about 6 inches (e.g., greater than or equal to about 1 inch to less than or equal to about 2 inches, greater than or equal to about 2 inches to less than or equal to about 3 inches, greater than or equal to about 3 inches to less than or equal to about 4 inches, greater than or equal to about 4 inches to less than or equal to about 5 inches, greater than or equal to about 5 inches to less than or equal to about 6 inches, or greater than or equal to about 6 inches to less than or equal to about 7 inches). The seventh height 644 may be greater than or equal to about 0.05 inches to less than or equal to about 0.5 inches (e.g., greater than or equal to about 0.05 inches to less than or equal to about 0.1 inches, greater than or equal to about 0.1 inches to less than or equal to about 0.25 inches, or greater than or equal to about 0.25 inches to less than or equal to about 0.5 inches). The eighth height 646 may be greater than or equal to about 0.05 inches to less than or equal to about 1 inch (e.g., greater than or equal to about 0.05 inches to less than or equal to about 0.1 inches, greater than or equal to about 0.1 inches to less than or equal to about 0.25 inches, greater than or equal to about 0.25 inches to less than or equal to about 0.5 inches, or greater than or equal to about 0.5 inches to less than or equal to about 1 inch). In certain aspects, the first and second flanges 580, 586 may be substantially identical and the plunger 414 may be substantially symmetric about a center plane (not shown) perpendicular to the longitudinal axis 416.

In various aspects, the plunger wall 568 may be substantially cylindrical. However, in various alternative aspects, the plunger wall 568 may define other shapes, such as a frusto-cone or a hexagonal prism, by way of example. In certain aspects, the plunger wall 568 may define an outer diameter or fourth dimension 648 of greater than or equal to about 0.125 inches to less than or equal to about 1 inch (e.g., greater than or equal to about 0.125 inches to less than or equal to about 0.1 inches, greater than or equal to about 0.1 inches to less than or equal to about 0.25 inches, greater than or equal to about 0.25 inches to less than or equal to about 0.5 inches, or greater than or equal to about 0.5 inches to less than or equal to about 1 inch). The plunger wall 568 may define fourth thickness 650 of greater than or equal to about 0.03125 inches to less than or equal to about 0.5 (e.g., greater than or equal to about 0.03125 inches to less than or equal to about 0.0625, greater than or equal to about 0.0625 inches to less than or equal to about 0.125, greater than or equal to about 0.125 inches to less than or equal to about 0.25, or greater than or equal to about 0.25 inches to less than or equal to about 0.5).

In various aspects, the aperture 566 may be substantially circular. The aperture 566 may define a diameter or fifth dimension 652 of greater than or equal to about 0.0625 inches to less than or equal to about 0.75 inches. For example, the fifth dimension 652 may be greater than or equal to about 0.0625 inches to less than or equal to about 0.125 inches, greater than or equal to about 0.125 inches to less than or equal to about 0.25 inches, greater than or equal to about 0.25 inches to less than or equal to about 0.5 inches, or greater than or equal to about 0.5 inches to less than or equal to about 0.75 inches.

Example dimensions are depicted in Table 2 below.

TABLE 2

| Dimension | Magnitude (inches) |
|---|---|
| First angle 474 | 45 |
| Second angle 480 | 45 |
| Third angle 494 | 35 |
| First dimension 544 | 0.5 |
| Second dimension 546 | 1.35 |
| Third dimension 548 | 0.5 |
| First height 610 | 3.0 |
| Third height 614 | 0.375 |
| First thickness 616 | 0.05-0.225 |
| Second thickness 618 | .05 |
| First diameter of curvature 620 | 5.536 |
| Third thickness 622 | 0.075 |

TABLE 2-continued

| Dimension | Magnitude (inches) |
|---|---|
| Fourth height 624 | 0.972 |
| First length 626 | 0.715 |
| Second length 628 | 0.385 |
| Third length 630 | 0.4 |
| Second radius of curvature 632 | 0.04 |
| Fifth height 640 | 2.075 |
| Sixth height 642 | 2.8 |
| Seventh height 644 | 0.145 |
| Eighth height 646 | 0.23 |
| Fourth dimension 648 | 0.36 |
| Fourth thickness 650 | 0.035 |
| Fifth dimension 652 | 0.345 |

The upper and lower portions 430, 432 of the outer tube 412 and the plunger 414 may each comprise a medical-grade material. In various aspects, the upper portion 430, the lower portion 432, and the plunger 414 each comprise a medical-grade plastic. Medical-grade plastics may include medical-grade thermoplastics or medical-grade thermosets. Suitable medical-grade thermoplastics may include an acrylonitrile butadiene styrene (ABS), an acetal copolymer (POM-C), an acetal homopolymer (POM-h), a polyethylene terephthalate polyester (PET-P), an ethylene chlorotrifluoroethylene (ECTFE) (e.g., HALAR®), a polybutylene terephthalate-polyester (PBT-P) (e.g., HYDREX®), a polyvinylidene fluoride (PVDF) (e.g., KYNAR®), a polyphenylene oxide (PPO) (e.g., NORYL®), a nylon, a polyetheretherketone (PEEK), a polycarbonate (PC), a thermoplastic polyethylene (PE) (e.g., a high-density thermoplastic polyethylele (HDPE), a low-density polyethylene (LDPE), an ultra-high-molecular-weight polyethylene (UHMWPE)), a polypropylene homopolymer, a polyphenylsulfone (PPSU), a polysulfone (PSU), a polyethersulfone (e.g., RADEL A®), a polyarylethersulfone (e.g., RADEL R®), a polytetrafluoroethylene (PTFE) (e.g., RULON® 641). In certain aspects, the medical-grade plastic may be a modified thermoplastic (e.g., FLUOROSINT®).

Figure 24:
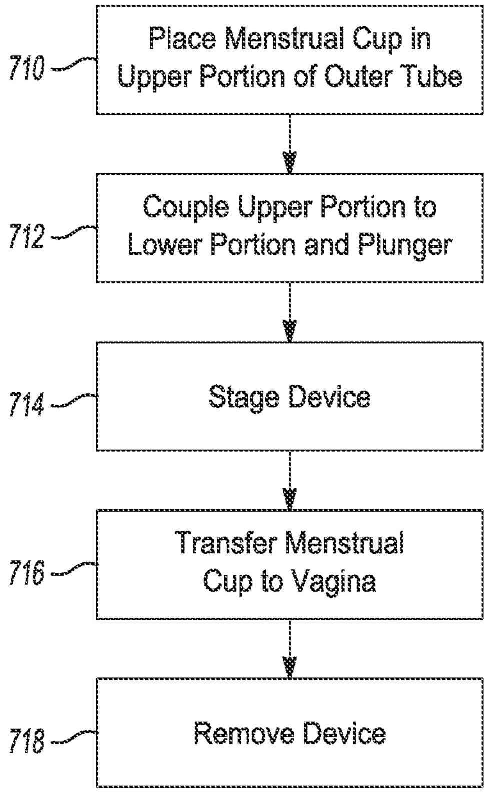
FIG. 24 is a flowchart depicting a method of placing the menstrual cup of FIG. 13 using the device of FIG. 14 according to various aspects of the present disclosure.

In various aspects, the present disclosure provides a method of placing a menstrual cup within a vagina. With reference to FIG. 24, a flow chart depicting a method of placing a menstrual cup according to various aspects of the present disclosure. Although the method is described with reference to the menstrual cup 310 of FIGS. 13A-13B and the device 410 of FIGS. 14-23, it will be appreciated that similar methods may be employed for other menstrual cups and/or devices.

At 710, the method includes staging the menstrual cup 310 in the upper portion 430 of the outer tube 412 of the device 410. With reference to FIGS. 25A-25B, the menstrual cup 310 is staged in the upper portion 430. The menstrual cup 310 may be placed into or close to alignment with the longitudinal axis 416 in the second direction 590 of the upper portion 430. The menstrual cup 310 may be moved in the first direction 472 toward the upper portion 430. As the menstrual cup 310 is moved into the upper interior region 444 (FIG. 25B), the body 312 (FIG. 25A) of the menstrual cup 310 engages the first distal surface 498 of the upper portion 430. The user may pull the stem 314 (FIG. 25A) in the first direction 472 to begin to deform the menstrual cup 310 from the expanded configuration to the collapsed configuration. More particularly, the protrusion 460 (FIG. 25B) of the upper portion 430 engages the outer surface 322 (FIG. 25A) of the menstrual cup 310 to form the indentation 326 (FIG. 25B).

When the menstrual cup 310 is fully disposed within the upper portion 430, the stem 314 and a portion of the body 312 may project in the first direction 472 with respect to the first intermediate end 440 (FIG. 25A) of the upper portion 430. The circumferential lip 324 of the menstrual cup 310 may project in the second direction 590 with respect to the first distal surface 498 of the upper portion 430. In certain aspects, only the circumferential lip 324 of the menstrual cup 310 extends past the first distal end 420 in the second direction 590. The protrusion 460 may be disposed at least partially within the indentation 326 of the menstrual cup 310.

Returning to FIG. 24, at 712, the method includes placing the outer tube 412 in the coupled configuration. With reference to FIG. 24C, the outer tube 412 is shown in the coupled configuration. More particularly, the upper portion 430 having the menstrual cup 310 disposed therein is coupled to the lower portion 432. The plunger 414 is slidingly engaged with the lower portion 432. The upper and lower portions 430, 432 may be coupled to one another, for example, by engaging the first and second pluralities of threads 500, 542 (FIGS. 21-22). The stem 314 of the menstrual cup 310 may be aligned with (i.e., along the longitudinal axis 416) or at least partially received in the aperture 566 of the plunger 414. The device 410 may be in the extended configuration.

At 714, the method includes staging the device 410. Staging the device includes placing the device 410 and/or the menstrual cup 310 at least partially within the vagina. In one example, at least a portion of the circumferential lip 324 of the menstrual cup 310 is inserted into the vagina. A portion of the device 410, such as the first distal end 420, may be inserted into the vagina to ensure proper alignment of the menstrual cup 310 in subsequent method steps.

At 716, the method further includes transferring the menstrual cup 310 into the vagina. With references to FIGS. 25D-25E, the user may grip the device 410 at the first base 540 and/or the peripheral wall 422. The user may translate the plunger 414 in the second direction 590, thereby pushing the menstrual cup 310 in the second direction 590 into the vagina. More particularly, the second distal surface 564 (FIGS. 19-20) of the plunger 414 engages the body 312 of the menstrual cup 310. As the menstrual cup 310 is translated in the second direction 590, the protrusion 460 (FIG. 25B) of the upper portion 430 disengages the body 312 of the menstrual cup 310 so that the menstrual cup 310 returns to the expanded configuration. FIG. 25D depicts the device 410 in an intermediate configuration between the extended and plunged configurations and the menstrual cup in an intermediate configuration between the collapsed and expanded configurations. FIG. 25E depicts the device 410 in the plunged configuration and the menstrual cup 310 in the expanded configuration. At 718, the method includes removing the device 410 from the vagina, if applicable. The menstrual cup 310 remains in the vagina.

In various aspects, the present disclosure provides a method of removing a menstrual cup from a vagina. With reference to FIG. 26, at 740, the method includes staging the device 410. Staging the device 410 includes placing the upper portion 430, without the lower portion 432 or the plunger 414, near or partially inserted into (e.g., the first distal end 420) the vagina. At 742, the method further includes transferring the menstrual cup 310 into the device 410. The menstrual cup 310 is transferred into the device in a similar manner as in step 710 of the method of FIG. 24, and as shown in FIGS. 24A-24B. More particularly, the user may grasp the stem 314 of the menstrual cup 310 and pull the stem in the first direction 472. The menstrual cup 310 slides into the upper portion 430 to engage the protrusion 460, gradually collapse to reduce suction and facilitate further removal, and slide into the upper portion 430. Both the menstrual cup 310 and the device 410 may be cleaned and reused.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A device for placement and removal of a menstrual cup, the device comprising:
- an outer component extending along a longitudinal axis between a first proximal end and a first distal end, the outer component comprising:
  - a peripheral wall including an interior surface,
  - a first interior region at least partially defined by the peripheral wall, and
  - a single radial protrusion extending radially inwardly from the interior surface toward the longitudinal axis, the single radial protrusion extending a majority of a distance between the interior surface and the longitudinal axis; and
- an inner component extending between a second proximal end and a second distal end, the inner component being disposed at least partially within the first interior region and slidable along the longitudinal axis with respect to the outer component.

2. The device of claim 1, wherein the outer component further comprises a rounded distal surface.

3. The device of claim 2, wherein the single radial protrusion is adjacent to the rounded distal surface.

4. The device of claim 1, wherein the single radial protrusion includes a first sloped surface and a second sloped surface.

5. The device of claim 4, wherein
- the first sloped surface defines a first length ranging from 0.25 inch to 1.5 inches, and
- the second sloped surface defines a second length ranging from 0.125 inch to 1.25 inches.

6. The device of claim 5, wherein
- the first length ranges from 0.5 inch to 1 inch, and
- the second length ranges from 0.25 inch to 0.5 inch.

7. The device of claim 4, wherein
- the first sloped surface defines a first angle with a plane perpendicular to the longitudinal axis,
- the first angle ranges from 20° to 75°, and
- the second sloped surface defines a second angle with the plane, and
- the second angle ranges from 20° to 65°.

8. The device of claim 7, wherein
- the first angle ranges from 40° to 50°, and
- the second angle ranges from 40° to 50°.

9. The device of claim 4, wherein
- the single radial protrusion further includes a third sloped surface,
- an undercut is defined between the interior surface and the third sloped surface, the third sloped surface defines an angle with a plane perpendicular to the longitudinal axis, and
the angle ranges from 100° to 170°.

10. The device of claim 1, wherein the second distal end includes a distal surface defining a notch configured to receive at least a portion of the single radial protrusion.

11. The device of claim 10, wherein
the device is configured to be moved between an extended configuration and a plunged configuration,
in the plunged configuration, the single radial protrusion is at least partially in the notch, and
in the extended configuration, the single radial protrusion is fully outside of the notch.

12. A device for placement and removal of a menstrual cup, the device comprising:
an outer component extending along a longitudinal axis between a first proximal end and a first distal end, the outer component comprising:
a peripheral wall,
a first interior region at least partially defined by the peripheral wall,
a protrusion extending from the peripheral wall toward the longitudinal axis, and
an interior surface defining a plurality of indentations; and
an inner component extending between a second proximal end and a second distal end, the inner component being disposed at least partially within the first interior region and slidable along the longitudinal axis with respect to the outer component, wherein
the outer component includes an upper portion and a lower portion separable from the upper portion,
the upper portion includes a first plurality of threads defining the plurality of indentations, and
the lower portion includes a second plurality of threads configured to engage the first plurality of threads to couple the lower portion to the upper portion.

13. The device of claim 12, wherein the plurality of indentations includes a plurality of circumferential grooves, a plurality of axial grooves, a plurality of dimples, knurling, or any combination thereof.

14. A device for placement and removal of a menstrual cup, the device comprising:
an outer component extending along a longitudinal axis between a first proximal end and a first distal end, the outer component comprising,
a peripheral wall including an interior surface,
a first interior region at least partially defined by the peripheral wall, and
a single protrusion extending radially inwardly from the interior surface toward the longitudinal axis, the single protrusion including a first sloped surface and a second sloped surface; and
an inner component extending between a second proximal end and a second distal end, the inner component being disposed at least partially within the first interior region and slidable along the longitudinal axis with respect to the outer component, wherein
the first sloped surface defines a first angle with a plane perpendicular to the longitudinal axis,
the first angle ranges from 20° to 75°, and
the second sloped surface defines a second angle with the plane, and
the second angle ranges from 20° to 65°.

15. The device of claim 14, wherein
the first angle ranges from 40° to 50°, and
the second angle ranges from 40° to 50°.

16. A device for placement and removal of a menstrual cup, the device comprising:
an outer component extending along a longitudinal axis between a first proximal end and a first distal end, the outer component comprising,
a peripheral wall including an interior surface,
a first interior region at least partially defined by the peripheral wall, and
a single radial protrusion extending radially inwardly from the interior surface toward the longitudinal axis, the single radial protrusion including a first sloped surface and a second sloped surface; and
an inner component extending between a second proximal end and a second distal end, the inner component being disposed at least partially within the first interior region and slidable along the longitudinal axis with respect to the outer component, wherein
the single radial protrusion further includes a third sloped surface,
an undercut is defined between the interior surface and the third sloped surface,
the third sloped surface defines an angle with a plane perpendicular to the longitudinal axis, and
the angle ranges from 100° to 170°.

17. A device for placement and removal of a menstrual cup, the device comprising:
an outer component extending along a longitudinal axis between a first proximal end and a first distal end, the outer component comprising,
a peripheral wall including an interior surface,
a first interior region at least partially defined by the peripheral wall, and
a single protrusion extending radially inwardly from the interior surface toward the longitudinal axis; and
an inner component extending between a second proximal end and a second distal end, the inner component being disposed at least partially within the first interior region and slidable along the longitudinal axis with respect to the outer component, wherein
the second distal end includes a distal surface defining a notch configured to receive at least a portion of the single radial protrusion,
the device is configured to be moved between an extended configuration and a plunged configuration,
in the plunged configuration, the single radial protrusion is at least partially in the notch, and
in the extended configuration, the single radial protrusion is fully outside of the notch.

* * * * *